US009532756B2

(12) United States Patent
Wakai et al.

(10) Patent No.: US 9,532,756 B2
(45) Date of Patent: Jan. 3, 2017

(54) MEDICAL IMAGE CONTROL SYSTEM AND MOBILE TERMINAL

(71) Applicant: Toshiba Medical Systems Corporation, Otawara-shi (JP)

(72) Inventors: Satoshi Wakai, Nasushiobara (JP); Satoshi Ikeda, Yaita (JP); Megumu Fukuda, Nasushiobara (JP); Takeshi Ezumi, Otawara (JP); Shinya Sugiyama, Nasushiobara (JP); Megumu Fujiwara, Sakura (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 134 days.

(21) Appl. No.: 14/161,471

(22) Filed: Jan. 22, 2014

(65) Prior Publication Data

US 2014/0133632 A1    May 15, 2014

Related U.S. Application Data

(63) Continuation of application No. PCT/JP2012/068473, filed on Jul. 20, 2012.

(30) Foreign Application Priority Data

Jul. 22, 2011  (JP) .................................. 2011-161225

(51) Int. Cl.
*A61B 6/00* (2006.01)
*A61B 5/00* (2006.01)
*G06F 19/00* (2011.01)

(52) U.S. Cl.
CPC . *A61B 6/44* (2013.01); *A61B 5/00* (2013.01); *A61B 5/0013* (2013.01); *A61B 5/742* (2013.01);
(Continued)

(58) Field of Classification Search
USPC .......................................................... 378/98
See application file for complete search history.

(56) References Cited

U.S. PATENT DOCUMENTS 6,369,812 B1 *  4/2002  Iyriboz ................. A61B 6/463
                                                         345/419
2007/0049815 A1 *  3/2007  Sanjay-Gopal ...... A61B 5/0002
                                                         600/407
(Continued)

FOREIGN PATENT DOCUMENTS

JP    2003-093354 A    4/2003
JP    2003-310592 A    11/2003
(Continued)

OTHER PUBLICATIONS

International Search Report mailed Oct. 9, 2012 for PCT/JP2012/068473 filed on Jul. 20, 2012 with English Translation.
(Continued)

*Primary Examiner* — Phillip A Johnston
*Assistant Examiner* — Hsien Tsai
(74) *Attorney, Agent, or Firm* — Oblon, McClelland, Maier & Neustadt, L.L.P.

(57) ABSTRACT

A medical image control system includes a medical image diagnostic apparatus and a mobile terminal. The medical image diagnostic apparatus includes a collecting unit, a distributing unit, and a reflecting unit. The collecting unit captures a subject based on predetermined image capturing conditions to collect time-series image data. The distributing unit distributes the time-series image data to the mobile terminal at least when the collecting unit collects the time-series image data. The reflecting unit receives control information and reflects the received control information to a process. The mobile terminal includes a replaying unit and a control information transmitting unit. The replaying unit receives the time-series image data distributed and replay the received time-series image data. The control information transmitting unit receives an operation related to the medical image diagnostic apparatus, and transmits control information indicating the received operation to the medical image diagnostic apparatus.

13 Claims, 14 Drawing Sheets

(52) U.S. Cl.
CPC ............ *A61B 6/462* (2013.01); *A61B 6/463* (2013.01); *A61B 6/464* (2013.01); *A61B 6/486* (2013.01); *A61B 6/503* (2013.01); *A61B 6/504* (2013.01); *A61B 6/5217* (2013.01); *A61B 6/548* (2013.01); *A61B 6/563* (2013.01); *G06F 19/321* (2013.01); *G06F 19/3406* (2013.01); *G06F 19/3418* (2013.01); *A61B 5/7285* (2013.01); *A61B 6/4441* (2013.01); *A61B 6/461* (2013.01); *A61B 6/469* (2013.01)

(56) References Cited

U.S. PATENT DOCUMENTS

| | | | | |
|---|---|---|---|---|
| 2009/0083074 | A1* | 3/2009 | Shioe | G06F 19/321 705/3 |
| 2010/0317420 | A1* | 12/2010 | Hoffberg | G06Q 30/0207 463/1 |

FOREIGN PATENT DOCUMENTS

| | | |
|---|---|---|
| JP | 2004-041605 A | 2/2004 |
| JP | 2004-081264 A | 3/2004 |
| JP | 2004-097783 A | 4/2004 |
| JP | 2005-034207 A | 2/2005 |
| JP | 2006-043298 A | 2/2006 |
| JP | 2006-198241 A | 8/2006 |
| JP | 2008-217294 A | 9/2008 |
| JP | 2009-075927 A | 4/2009 |

OTHER PUBLICATIONS

International Written Opinion mailed Oct. 9, 2012 for PCT/JP2012/068473 filed on Jul. 20, 2012.
Fujifilm Corporation, Enkaku Gazo Shindan Chiryo Hojyo Sistemu, i-Stroke (Telediagnostic Imaging Support System, i-Stroke), Jun. 16, 2011, online, <URL: http://www.fujifilm.co.jp/corporate/news/articleffnr_0519.html>.

* cited by examiner

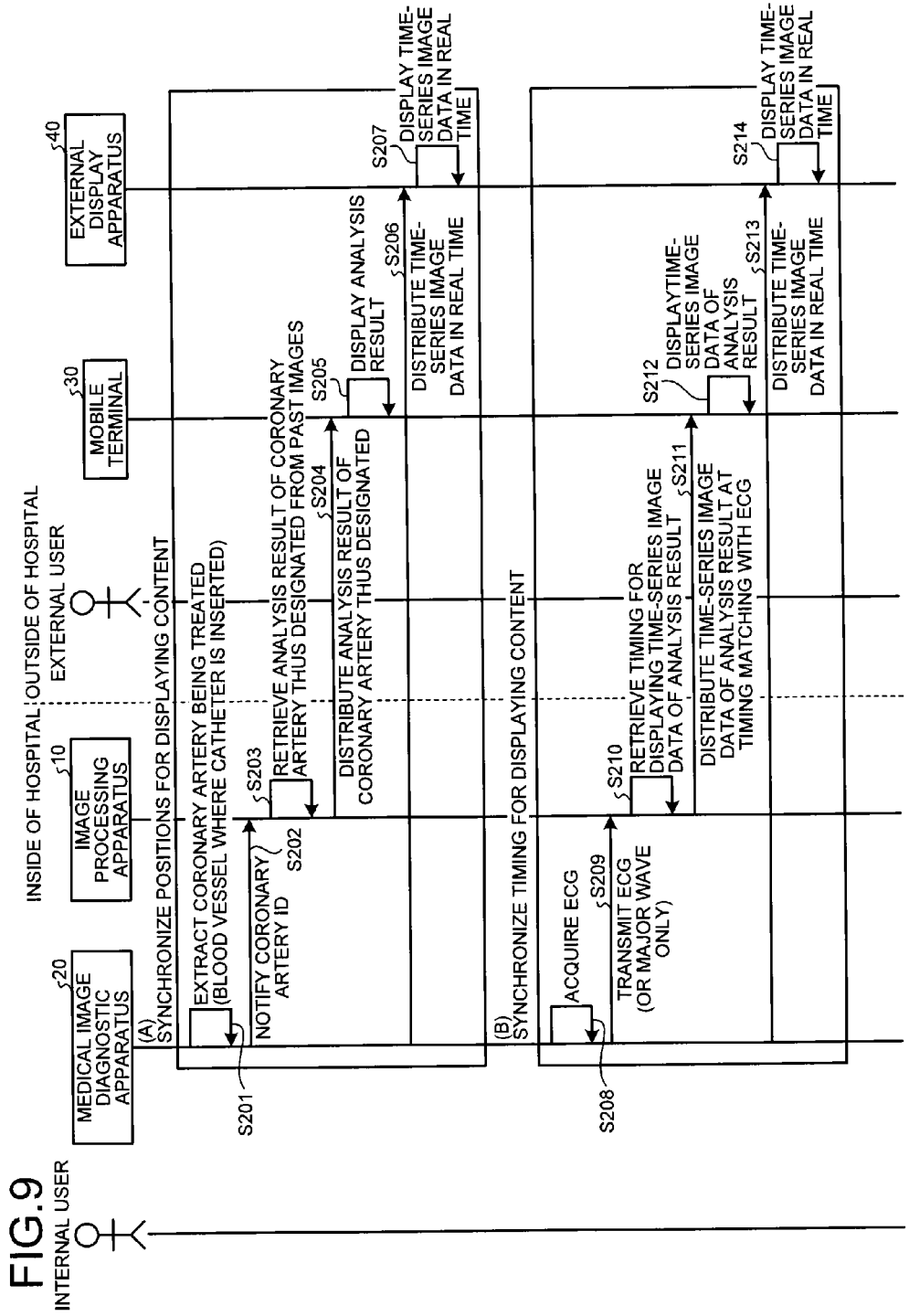

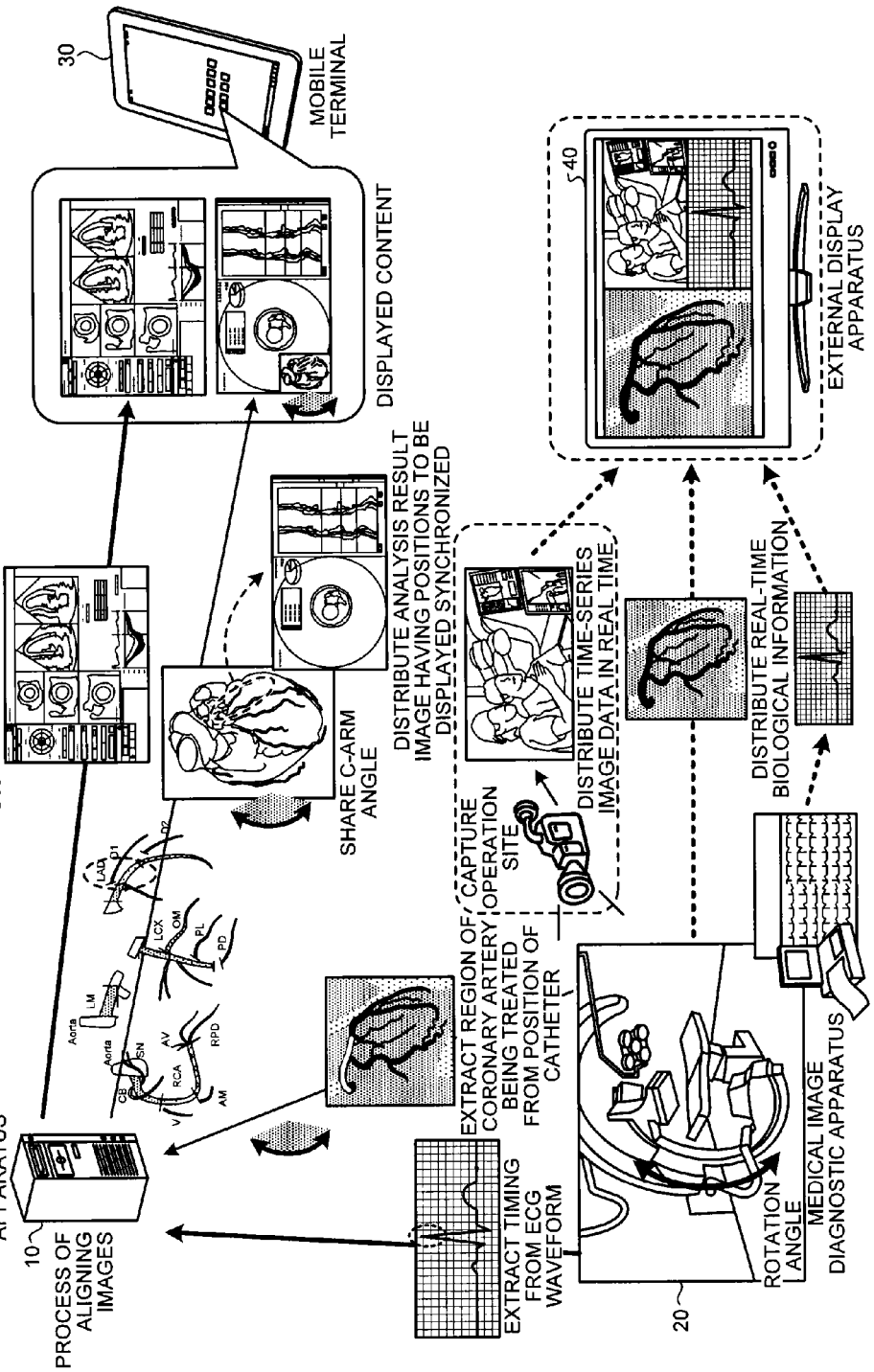

FIG.11

| RISK LEVEL | FUNCTION | LIMITATION ON REMOTE USER OPERATIONS |
|---|---|---|
| A | START CAPTURING IMAGE | OPERATION NOT PERMITTED |
| B | CHANGE CONDITION DURING IMAGE CAPTURING (E.G., SET POSITION/ DIRECTION OF C-ARM) | OPERATION PERMITTED, PROVIDED THAT RESULT IS REFLECTED AFTER LOCAL USER'S APPROVAL |
| C | MAKE OPERATIONS ON STORED IMAGE (E.G., LUMINANCE CONVERSION, GEOMETRIC TRANSFORMATION, IMAGE PROCESSING) | OPERATION PERMITTED |

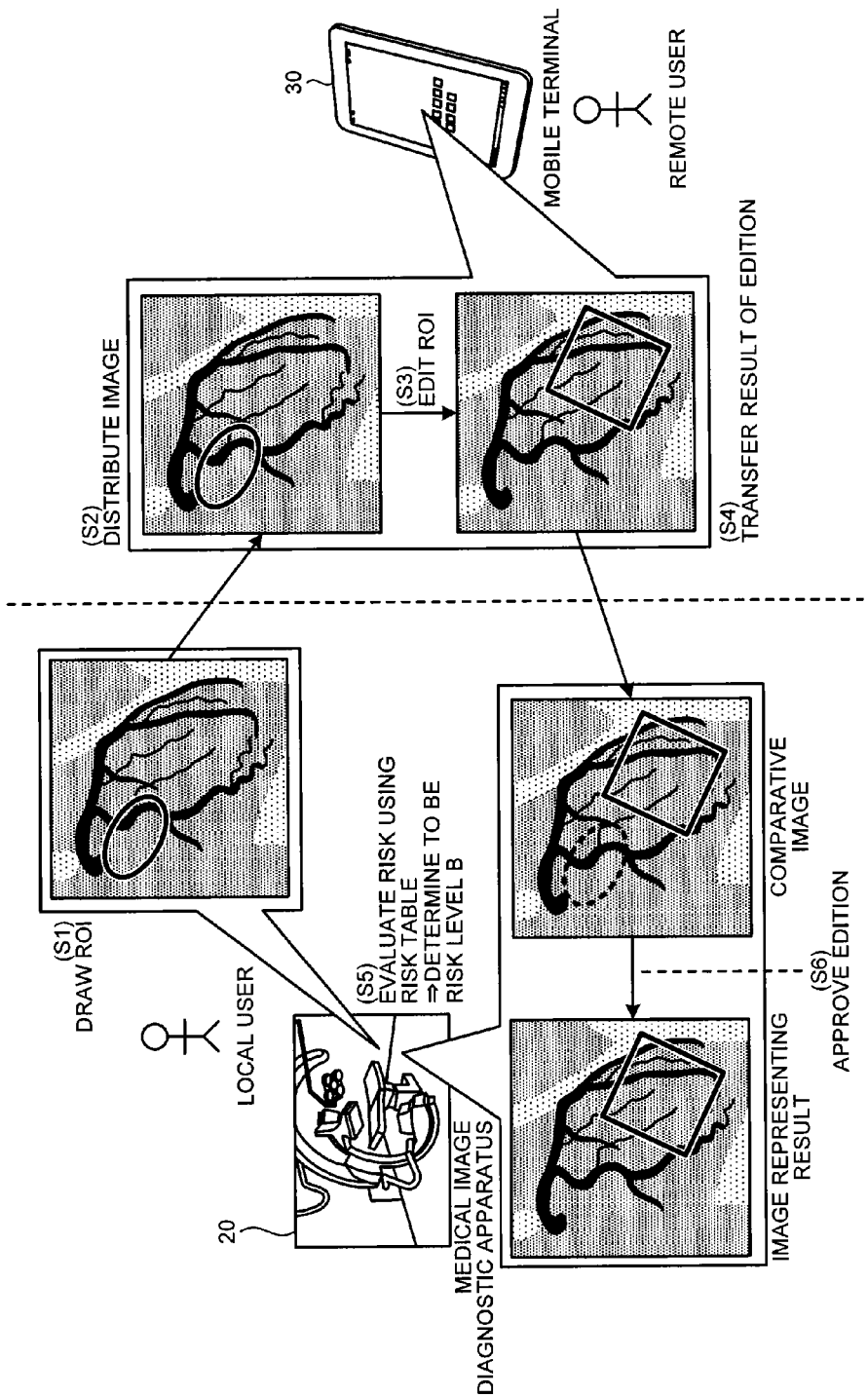

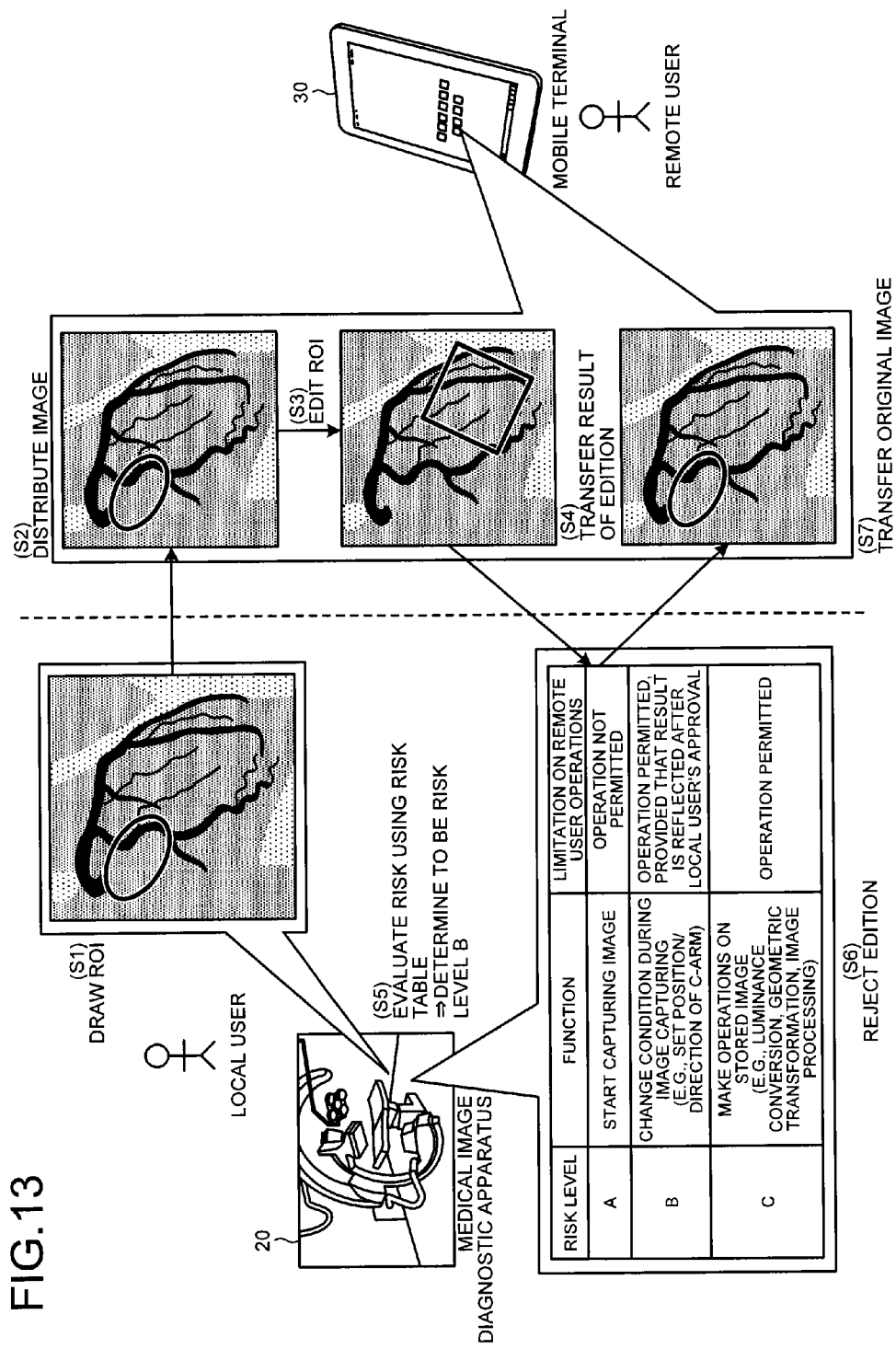

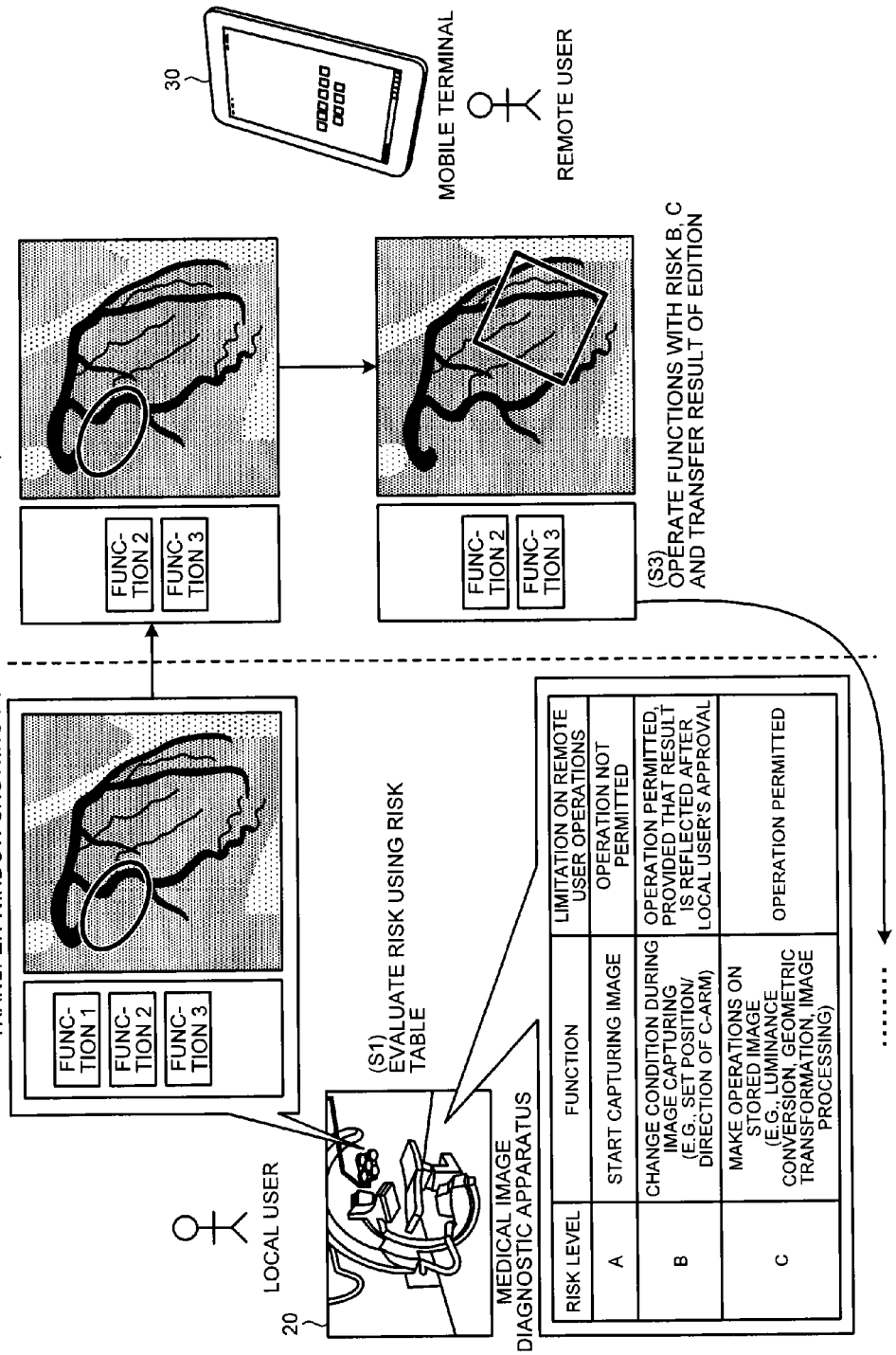

MEDICAL IMAGE CONTROL SYSTEM AND MOBILE TERMINAL

CROSS-REFERENCE TO RELATED APPLICATIONS

This application is a continuation of International Application No. PCT/JP2012/068473, filed on Jul. 20, 2012 which claims the benefit of priority of the prior Japanese Patent Application No. 2011-161225, filed on Jul. 22, 2011, the entire contents of which are incorporated herein by reference.

FIELD

Embodiments described herein relate generally to a medical image control system and a mobile terminal.

BACKGROUND

Recently, doctor shortage has become a serious problem in medical institutions, and medical support systems have emerged as one of countermeasures. A remote medical support system is a system that supports a medical intervention in a hospital, mainly by providing a remote access to an apparatus installed in (hereinafter, referred to as "in-hospital") the hospital.

When an emergency case occurs in the midnight, for example, conventionally, it has been common for doctors on duty to rush into the hospital despite being the middle of the night, or to give instructions to staffs in the hospital over a telephone providing only voice data. The emergence of remote medical support systems has enabled doctors to access an in-hospital apparatus from their home, business trip destinations, or the like, and to view information such as image data using a personal computer (PC). As mobile terminals such as mobile phones or tablet PCs have become more widespread, coming to be desired is a system that can support a medical intervention in the hospital while a doctor is traveling on a car or a bullet train, for example, without any limitation to homes and business trip destinations.

BRIEF DESCRIPTION OF THE DRAWINGS

FIG. 9 is a sequence chart illustrating an example of a process in the second embodiment;

FIG. 10 is a schematic for explaining a variation of the second embodiment;

FIG. 11 is a schematic for explaining a risk table in a third embodiment;

FIG. 12 is a schematic for explaining a limitation in a function made available for remote control in the third embodiment;

FIG. 13 is a schematic for explaining a limitation in a function made available for remote control in the third embodiment; and FIG. 14 is a schematic for explaining a variation of a limitation in functions made available for remote control in the third embodiment.

DETAILED DESCRIPTION

A medical image control system includes a medical image diagnostic apparatus and a mobile terminal. The medical image diagnostic apparatus includes a collecting unit, a distributing unit, and a reflecting unit. The collecting unit captures a subject based on predetermined image capturing conditions to collect time-series image data. The distributing unit distributes the time-series image data to the mobile terminal at least when the collecting unit collects the time-series image data. The reflecting unit receives control information transmitted by the mobile terminal, and reflects the received control information to a process performed by the medical image diagnostic apparatus. The mobile terminal includes a replaying unit and a control information transmitting unit. The replaying unit receives the time-series image data distributed by the distributing unit, and replays the received time-series image data. The control information transmitting unit receives an operation related to the medical image diagnostic apparatus, and transmits control information indicating the received operation to the medical image diagnostic apparatus.

Embodiments of a medical image control system and a mobile terminal will now be explained in detail with reference to the accompanying drawings.

First Embodiment

Figure 1:
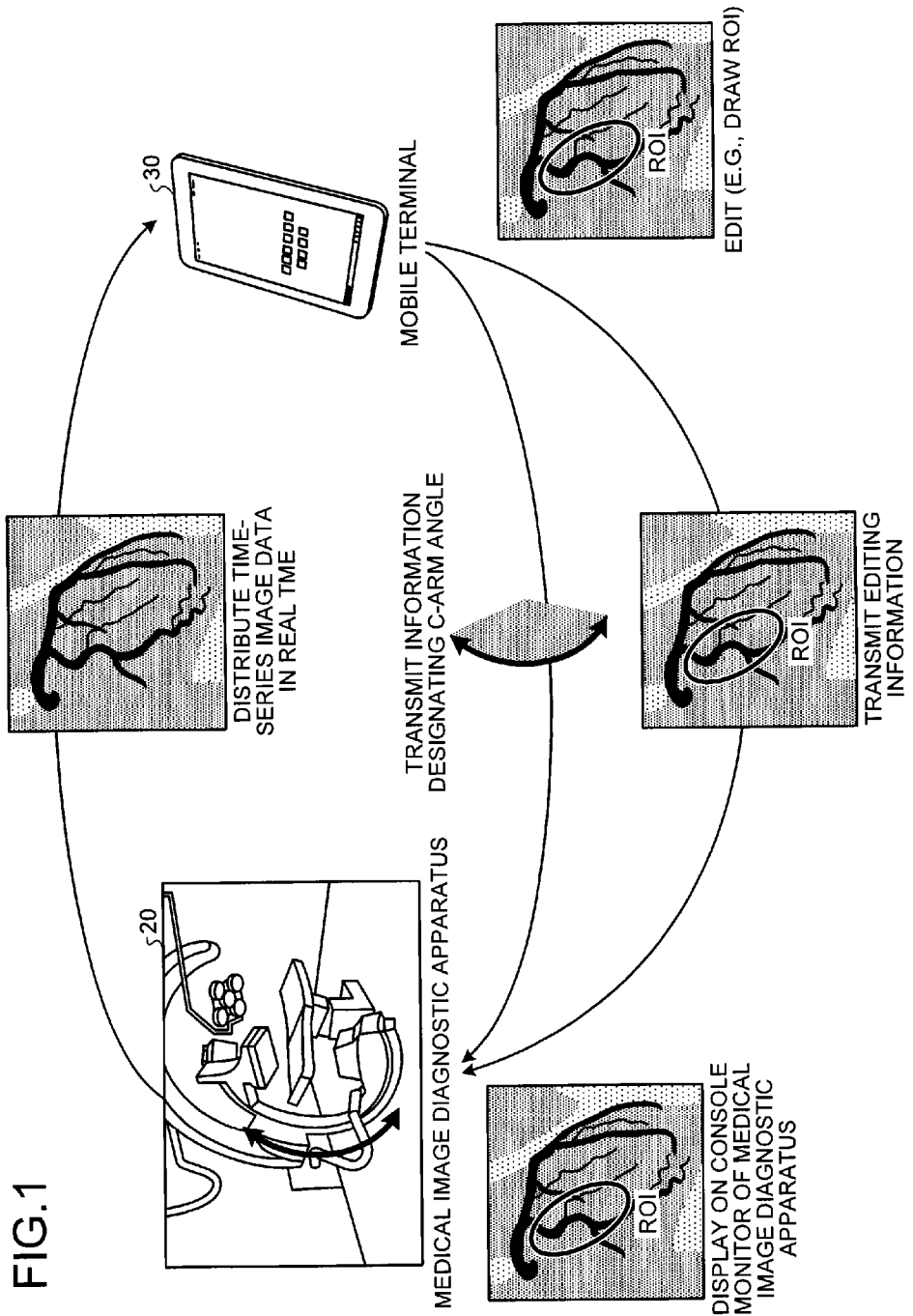
FIG. 1 is a schematic for explaining the concept of a medical image control system according to a first embodiment.

FIG. 1 is a schematic for explaining the concept of a medical image control system according to a first embodiment. As illustrated in FIG. 1, the medical image control system according to the first embodiment includes a medical image diagnostic apparatus 20 and a mobile terminal 30. The medical image diagnostic apparatus 20 distributes time-series image data to the mobile terminal 30 in real time. In other words, the medical image diagnostic apparatus 20 captures a subject to collect time-series image data, and distributes the time-series image data to the mobile terminal 30 at least when the medical image diagnostic apparatus 20 collects the time-series image data.

In the first embodiment, the mobile terminal 30 receives an operation related to the medical image diagnostic apparatus 20, and transmits control information indicating the received operation to the medical image diagnostic apparatus 20. For example, when the medical image diagnostic apparatus 20 is an X-ray diagnostic apparatus, the mobile terminal 30 receives an operation for setting a C-arm angle as an operation related to an image capturing condition for the medical image diagnostic apparatus 20, as illustrated in FIG. 1, and transmits the received information designating the angle to the medical image diagnostic apparatus 20.

Upon receiving the setting information, the medical image diagnostic apparatus 20 reflects the C-arm angle designated by the mobile terminal 30 to the image capturing condition, and then captures images.

As another example, the mobile terminal 30 receives an operation editing the time-series image data (e.g., an X-ray image) distributed by the medical image diagnostic apparatus 20, as illustrated in FIG. 1 (for example, an operation of drawing a region-of-interest (ROI)), transmits the editing information thus received to the medical image diagnostic apparatus 20. Upon receiving the editing information, the medical image diagnostic apparatus 20 reflects the received editing information to the time-series image data being replayed by the medical image diagnostic apparatus 20. For example, the medical image diagnostic apparatus 20 displays the ROI drawn on the mobile terminal 30 on the time-series image data being replayed on a console monitor included in the medical image diagnostic apparatus 20.

Figure 2:
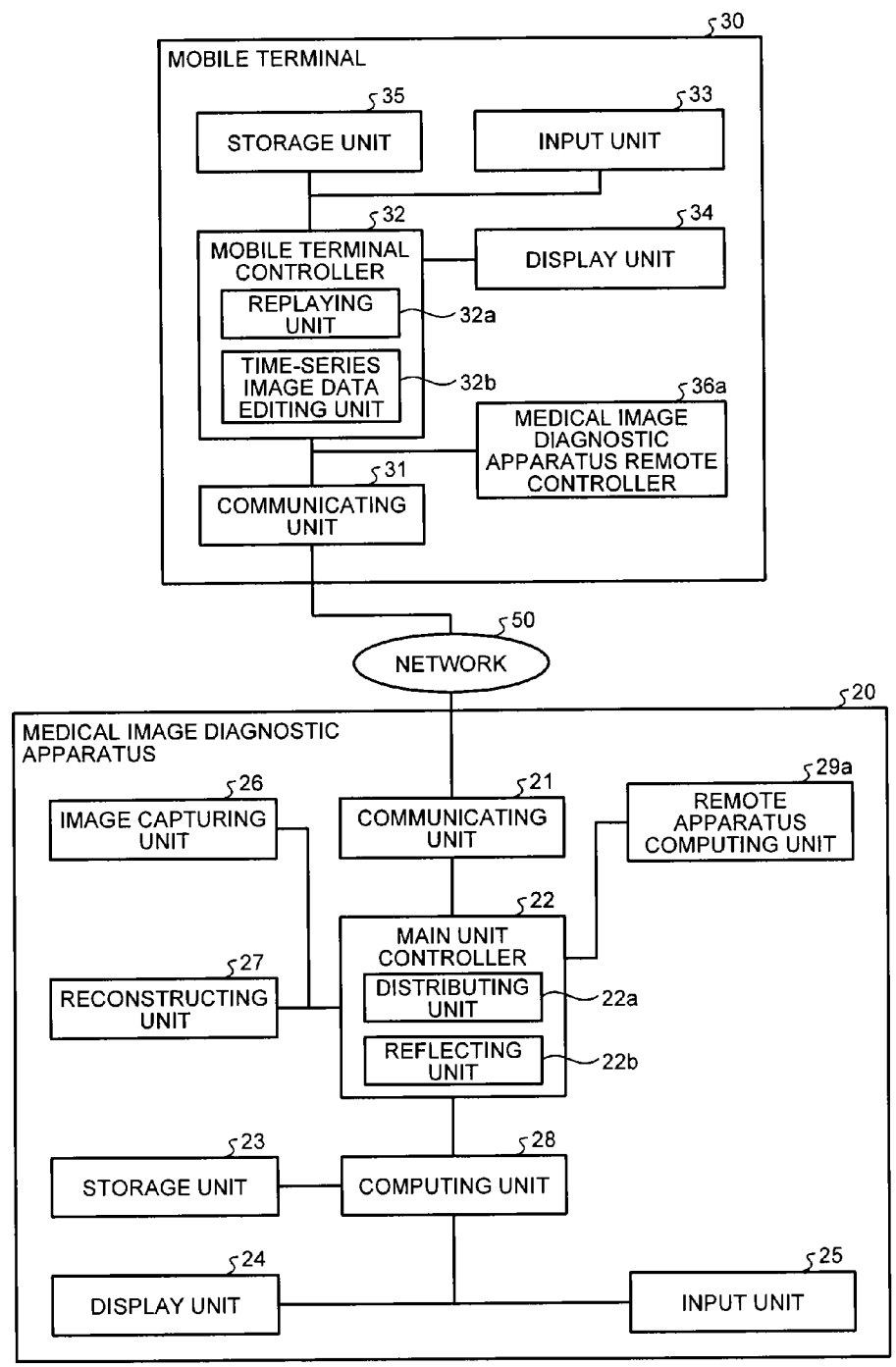
FIG. 2 is a schematic for explaining an exemplary configuration of the medical image control system according to the first embodiment.

FIG. 2 is a schematic for explaining an exemplary configuration of the medical image control system according to the first embodiment. As illustrated in FIG. 2, the medical image diagnostic apparatus 20 and the mobile terminal 30 are connected over a network 50. For example, the mobile terminal 30 accessible to the Internet over a wireless local area network (LAN), a mobile phone network, or the like accesses the medical image diagnostic apparatus 20 deployed in an in-hospital LAN over the Internet. When the medical image control system is realized in an environment closed within the hospital, the mobile terminal 30 accesses the medical image diagnostic apparatus 20 via the in-hospital LAN, for example.

The medical image diagnostic apparatus 20 includes a communicating unit 21, a main unit controller 22, a storage unit 23, a display unit 24, an input unit 25, an image capturing unit 26, a reconstructing unit 27, a computing unit 28, and a remote apparatus computing unit 29a.

The communicating unit 21 is an interface on the medical image diagnostic apparatus 20 connecting to the in-hospital LAN. The communicating unit 21 connects to the hospital LAN or to the Internet external to the hospital via network devices such as a hub, and communicates with the mobile terminal 30.

The main unit controller 22 is an electronic circuit such as a central processing unit (CPU) or a micro-processing unit (MPU), or an integrated circuit such as an application specific integrated circuit (ASIC) or a field programmable gate array (FPGA), and controls the overall processing units included in the medical image diagnostic apparatus 20. The main unit controller 22 includes a distributing unit 22a and a reflecting unit 22b.

The distributing unit 22a distributes time-series image data collected by the image capturing unit 26 and then generated by the reconstructing unit 27 and the computing unit 28 to the mobile terminal 30 in real time using a push-based technology. In other words, the distributing unit 22a distributes the time-series image data to the mobile terminal 30 at least when the image capturing unit 26 collects the time-series image data. The distributing unit 22a may be realized using a known streaming technology (e.g., the Real Time Streaming Protocol (RTSP)) or a progressive download technology.

The reflecting unit 22b receives control information transmitted from the mobile terminal 30, and reflects the received control information to a process performed by the medical image diagnostic apparatus 20. For example, when the reflecting unit 22b receives information for setting an image capturing condition (for example, information designating an angle of the C-arm) from the mobile terminal 30, the reflecting unit 22b reflects the setting information thus received to the image capturing condition used by the medical image diagnostic apparatus 20. As another example, when the reflecting unit 22b receives information for editing time-series image data (for example, information for editing an ROI) from the mobile terminal 30, the reflecting unit 22b reflects the editing information thus received to the time-series image data replayed by the medical image diagnostic apparatus 20.

The storage unit 23 is a hard disk, a semiconductor memory, or the like, and stores therein various types of information in the medical image diagnostic apparatus 20. For example, the storage unit 23 stores therein image capturing conditions used by the image capturing unit 26, captured data collected by the image capturing unit 26, image data generated by the reconstructing unit 27, and image data generated by the computing unit 28, for example.

The display unit 24 is a monitor, and displays various types of information in the medical image diagnostic apparatus 20 as a console monitor of the medical image diagnostic apparatus 20. For example, the display unit 24 displays a graphical user interface (GUI) for receiving an operation for the medical image diagnostic apparatus 20, and image data generated by the reconstructing unit 27 and the computing unit 28 while images are being captured or after the images are captured. The input unit 25 is a mouse, a keyboard, a trackball, and the like, and receives an operation to the medical image diagnostic apparatus 20 from an operator.

The image capturing unit 26 captures an image of a subject by controlling the hardware of the medical image diagnostic apparatus 20 based on predetermined image capturing conditions to collect captured data. For example, when the medical image diagnostic apparatus 20 is an X-ray diagnostic apparatus, when a pressing operation on a button for starting capturing an image is received from an operator, the image capturing unit 26 captures images of the subject by controlling the C-arm and the X-ray tube, and receives X rays passed through the subject by controlling a detector. The image capturing unit 26 according to the first embodiment captures a subject, and collects captured time-series image data.

The reconstructing unit 27 generates image data by reconstructing captured data collected by the image capturing unit 26. For example, the reconstructing unit 27 reconstructs time-series image data from captured time-series image data collected by the image capturing unit 26 to generate time-series image data.

The computing unit 28 applies image processing to the image data reconstructed by the reconstructing unit 27. For example, when the medical image diagnostic apparatus 20 is an X-ray computed tomography (CT) apparatus, the computing unit 28 converts image data being slice images reconstructed by the reconstructing unit 27 into volume data, and applies image processing such as aligning pieces of image data and extracting specific regions, and then performs a volume rendering process.

When different operations are received from the medical image diagnostic apparatus 20 and from the mobile terminal 30 and received operations are to be processed in parallel, the remote apparatus computing unit 29a dedicatedly performs a process for the mobile terminal 30. For example, when different operations are received from the display unit 24 of the medical image diagnostic apparatus 20 (console monitor; also referred to as a local display) and from a display unit 34 of the mobile terminal 30 (remote display), and the received operations are to be processed in parallel, the remote apparatus computing unit 29a dedicatedly performs a process for the remote display. In such a case, different content is displayed on the local display and the remote display, and different operations are performed in parallel, for example. When the medical image diagnostic apparatus 20 is enabled to be controlled from both of the local display and the remote display, the local display and the remote display may be controlled so that only one of the local display and the remote display has the control. For example, when the mobile terminal 30 has the control, any operation is not permitted on the local display for the time-series image data collected by and stored in the medical image diagnostic apparatus 20, and only operations on the remote display are valid.

The mobile terminal 30 is a PC, a tablet PC, or a personal digital assistant (PDA), a mobile phone, or the like. As illustrated in FIG. 2, the mobile terminal 30 includes a communicating unit 31, a mobile terminal controller 32, an input unit 33, a display unit 34, a storage unit 35, and a medical image diagnostic apparatus remote controller 36a.

The communicating unit 31 is an interface on the mobile terminal 30 connecting to the in-hospital LAN or the Internet via a wireless access point or the like, and communicates with the medical image diagnostic apparatus 20. The mobile terminal controller 32 is an electronic circuit such as a CPU or an MPU, or an integrated circuit such as an ASIC or an FPGA, and controls the overall processing units included in the mobile terminal 30. The mobile terminal controller 32 includes a replaying unit 32a and a time-series image data editing unit 32b.

The replaying unit 32a receives time-series image data distributed by the medical image diagnostic apparatus 20, and replays the received time-series image data on the display unit 34 in real time. The time-series image data editing unit 32b receives an editing operation for time-series image data being replayed by the replaying unit 32a, and reflects the received editing operation to the time-series image data replayed by the replaying unit 32a. For example, when an operation of drawing an ROI for time-series image data currently being replayed is received, the time-series image data editing unit 32b displays the ROI thus received on the time-series image data being displayed. An editing operation received by the time-series image data editing unit 32b may also be stored in the storage unit 35.

The input unit 33 is a touch panel, a special button, a gyrosensor, and the like, and receives an operation for the mobile terminal 30 from an operator. The display unit 34 is a liquid crystal panel, for example, and displays various types of information in the mobile terminal 30 as a display unit of the mobile terminal 30 (remote display). For example, the display unit 34 displays image data received from the medical image diagnostic apparatus 20 and a GUI for receiving an operation for the medical image diagnostic apparatus 20, for example. When the input unit 33 is a touch panel, the input unit 33 may also function as the display unit 34. The storage unit 35 is a hard disk, a semiconductor memory, or the like, and stores therein various types of information in the mobile terminal 30.

The medical image diagnostic apparatus remote controller 36a receives an operation related to the medical image diagnostic apparatus 20, and controls the medical image diagnostic apparatus 20 remotely by transmitting control information indicating the received operation to the medical image diagnostic apparatus 20. For example, the medical image diagnostic apparatus remote controller 36a receives an operation related to an image capturing condition (for example, an operation designating the angle of the C-arm), and transmits the information for setting the received image capturing condition to the medical image diagnostic apparatus 20. As another example, the medical image diagnostic apparatus remote controller 36a receives editing information for time-series image data (for example, a drawing operation of an ROI), and transmits the received editing information to the medical image diagnostic apparatus 20. The medical image diagnostic apparatus 20 receives the editing information transmitted by the mobile terminal 30, and reflects the editing information to the time-series image data currently being replayed on the local display or saves the editing information to the storage unit 23 as a background process, for example. The editing information may also be stored in the storage unit 35 in the mobile terminal 30.

Figure 3:
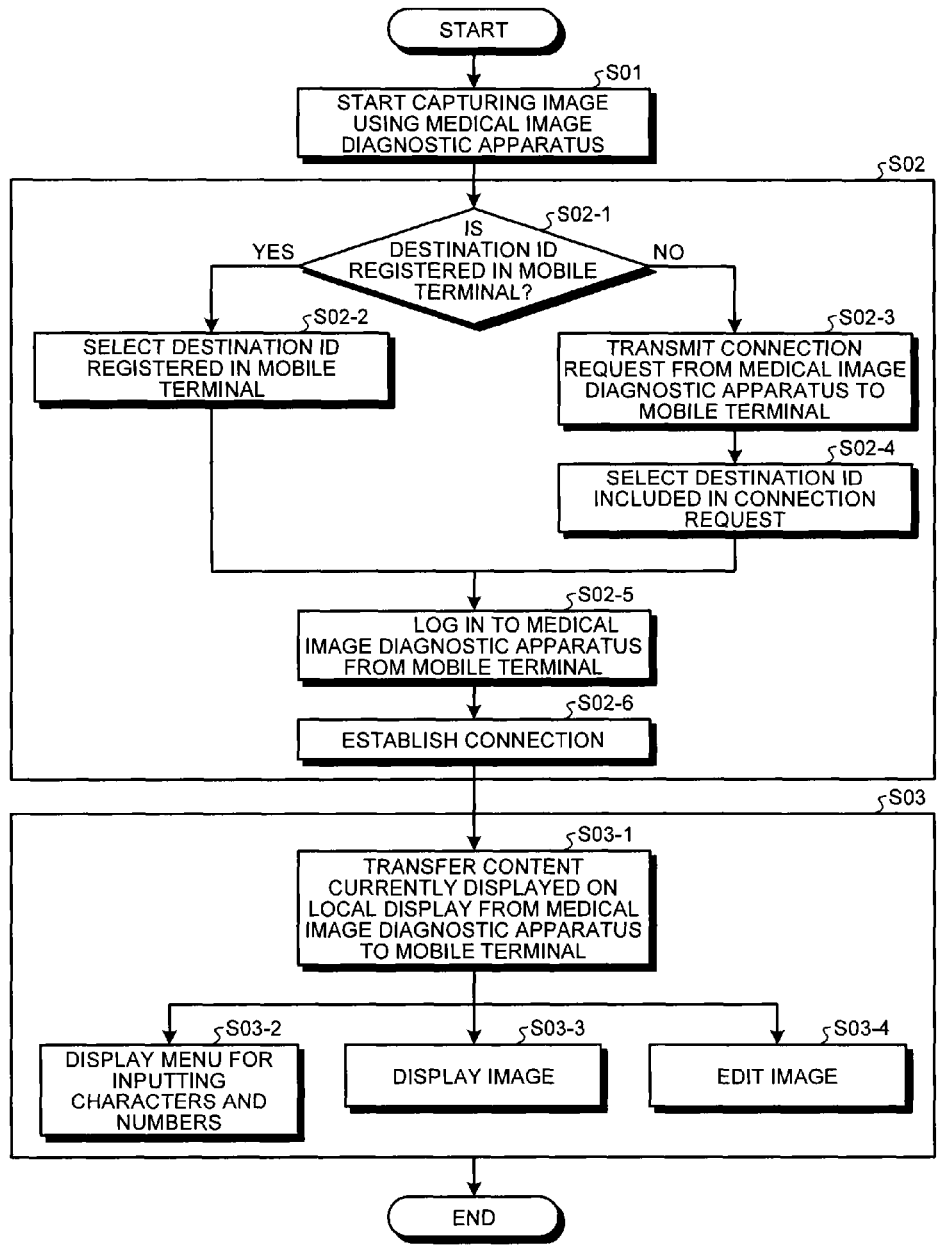
FIG. 3 is a flowchart illustrating an example of a process performed in the first embodiment.

FIG. 3 is a flowchart illustrating an example of the process performed in the first embodiment. As illustrated in FIG. 3, to begin with, in the medical image control system according to the first embodiment, an examination or treatment is started, and an image starts being captured by the medical image diagnostic apparatus 20 (Step S01).

From the viewpoint of security, a mutual authentication is performed between the medical image diagnostic apparatus 20 and the mobile terminal 30 (Step S02). For example, the medical image diagnostic apparatus 20 acquires an identification from the mobile terminal 30 and authenticates if the counterpart is a trusted apparatus and vice versa.

To explain an example, a user of the mobile terminal 30 checks if the destination identification (ID) (the ID of the medical image diagnostic apparatus 20) is registered (Step S02-1). If the destination ID is registered (Yes at Step S02-1), the user of the mobile terminal 30 makes an operation for selecting the registered destination ID (Step S02-2). If the destination ID is not registered (No at Step S02-1), the user of the medical image diagnostic apparatus 20 makes an operation so that a connection request is transmitted (e.g., so that an email is transmitted) from the medical image diagnostic apparatus 20 to the mobile terminal 30 (Step S02-3). The user of the mobile terminal 30 then makes an operation for selecting the destination ID included in the connection request (Step S02-4).

In response to the user of the mobile terminal 30 selecting the destination ID, an uniform resource locator (URL) associated with the destination ID is accessed, for example, allowing the mobile terminal 30 to log-in the medical image diagnostic apparatus 20 (Step S02-5), and a connection is established between the medical image diagnostic apparatus 20 and the mobile terminal 30 (Step S02-6). The process of establishing a connection between the medical image diagnostic apparatus 20 and the mobile terminal 30 is not limited to the one described above, and may be realized using other known authentication technologies.

The distributing unit 22a in the medical image diagnostic apparatus 20 then transmits time-series image data or other types of content to the mobile terminal 30 (Step S03). For example, the distributing unit 22a transfers the content currently being replayed (or displayed) on the local display to the mobile terminal 30 (Step S03-1). A known streaming technology or progressive download technology, for example, is used in distributing time-series image data, as mentioned earlier.

To explain using a specific example, the distributing unit 22a distributes a menu for inputting an image capturing condition to the mobile terminal 30, and the menu is displayed on the remote display (Step S03-2). The user of the mobile terminal 30 enters an image capturing condition, such as a current or a voltage for an X-ray tube, for example, by entering a number or characters in the menu, for example. The medical image diagnostic apparatus remote controller 36a in the mobile terminal 30 then transmits the information for setting the image capturing condition entered by the user to the medical image diagnostic apparatus 20. The medical image diagnostic apparatus 20 reflects the image capturing condition, and then captures an image. In this manner, image capturing performed by the medical image diagnostic apparatus 20 can be controlled from the mobile terminal 30.

In addition, the distributing unit 22a transmits time-series image data currently being replayed on the local display to the mobile terminal 30, and the same time-series image data on the local display is replayed on the remote display (Step S03-3). The user of the mobile terminal 30 then enters an image capturing condition such as a direction in which an image is captured by dragging a mouse on the time-series image data or by tilting the mobile terminal 30, for example. The medical image diagnostic apparatus remote controller 36a included in the mobile terminal 30 then transmits information for setting the image capturing condition entered by the user to the medical image diagnostic apparatus 20. The medical image diagnostic apparatus 20 reflects the image capturing condition, and captures an image. In this manner, image capturing performed by the medical image diagnostic apparatus 20 can be controlled from the mobile terminal 30.

When the distributing unit 22a transmits time-series image data other than the time-series image data currently being displayed on the local display (e.g., time-series image data stored in the medical image diagnostic apparatus 20) to the mobile terminal 30, the time-series image data other than the time-series image data currently on the local display is displayed on the remote display (Step S03-4). The user of the mobile terminal 30 then draws an ROI on the time-series image data, for example. The time-series image data editing unit 32b in the mobile terminal 30 stores the editing information entered by the user in the storage unit 35 in the mobile terminal 30, or the medical image diagnostic apparatus remote controller 36a transmits the editing information entered by the user to the medical image diagnostic apparatus 20. In this manner, replaying conditions for replaying time-series image data distributed by the medical image diagnostic apparatus 20 can be specified independently from conditions for replaying time-series image data currently being replayed by the medical image diagnostic apparatus 20, and the time-series image data can be edited on the mobile terminal 30.

Advantageous Effects Achieved by First Embodiment

In the manner described above, according to the first embodiment, time-series image data currently being captured by the medical image diagnostic apparatus 20 can be replayed on the mobile terminal 30 in real time. Furthermore, according to the first embodiment, conditions for capturing images in the medical image diagnostic apparatus 20 can be controlled from the mobile terminal 30. Furthermore, according to the first embodiment, time-series image data distributed by the medical image diagnostic apparatus 20 can be edited on the mobile terminal 30. The medical image control system does not necessarily need to include all of these functions, and may include some of these functions. For example, the system may only distribute time-series image data to the mobile terminal 30 in real time, without receiving any control for the image capturing conditions or any edition from the mobile terminal 30. Furthermore, operations permitted on the mobile terminal 30 may be controlled based on an access level defined for each user, for example.

Second Embodiment

Figure 4:
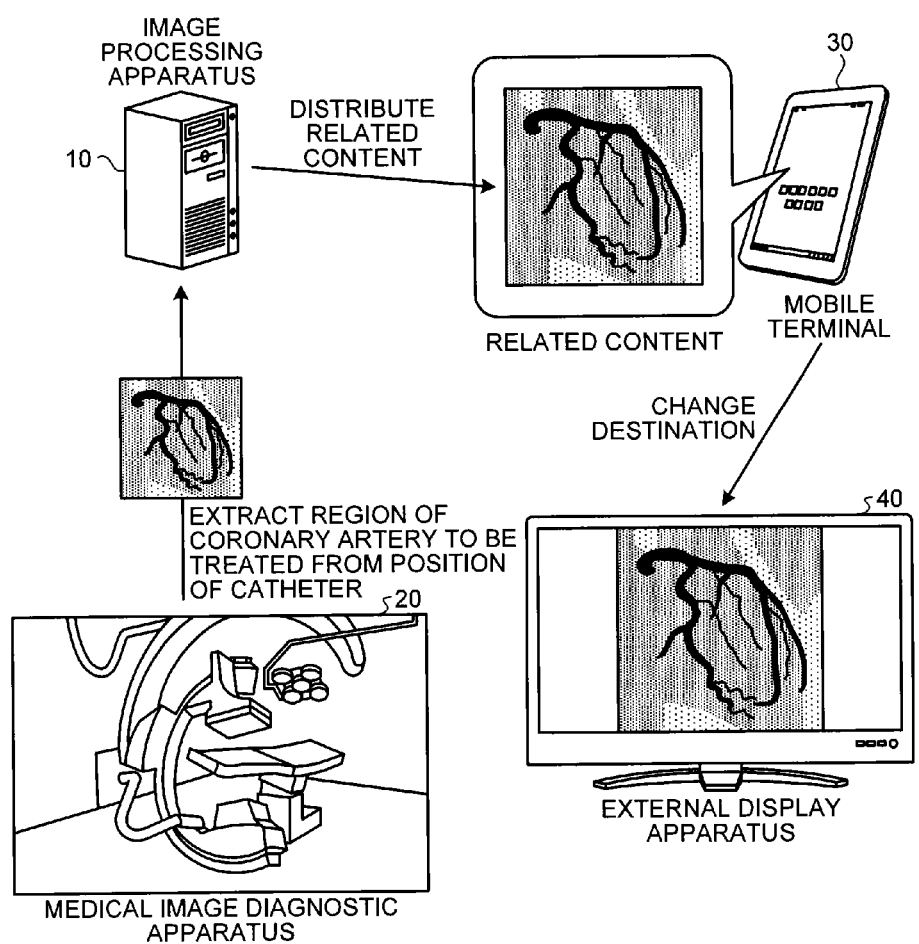
FIG. 4 is a schematic for explaining the concept of a medical image control system according to a second embodiment.
Figure 5:
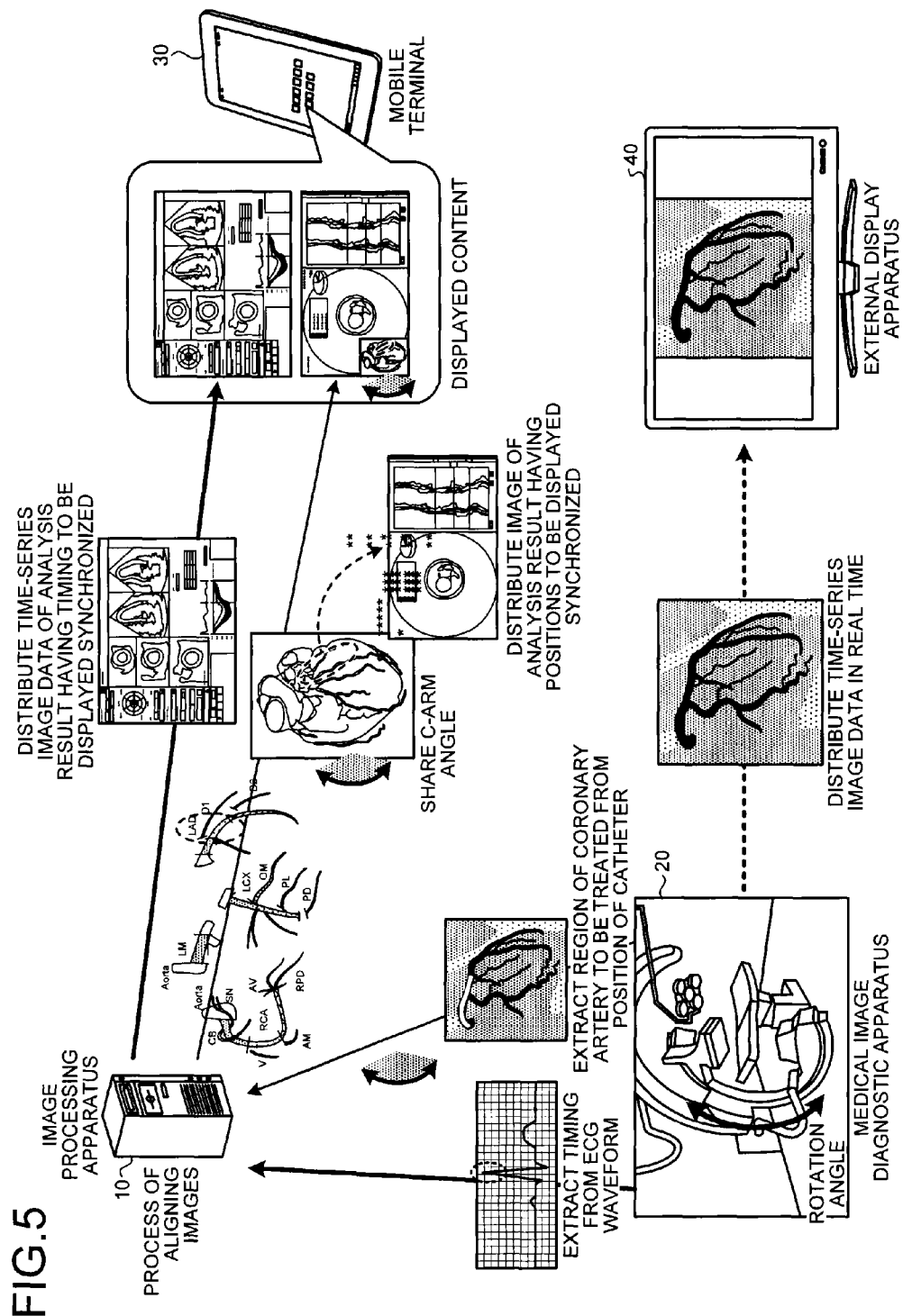
FIG. 5 is a schematic for explaining the concept of the medical image control system according to the second embodiment.
Figure 6:
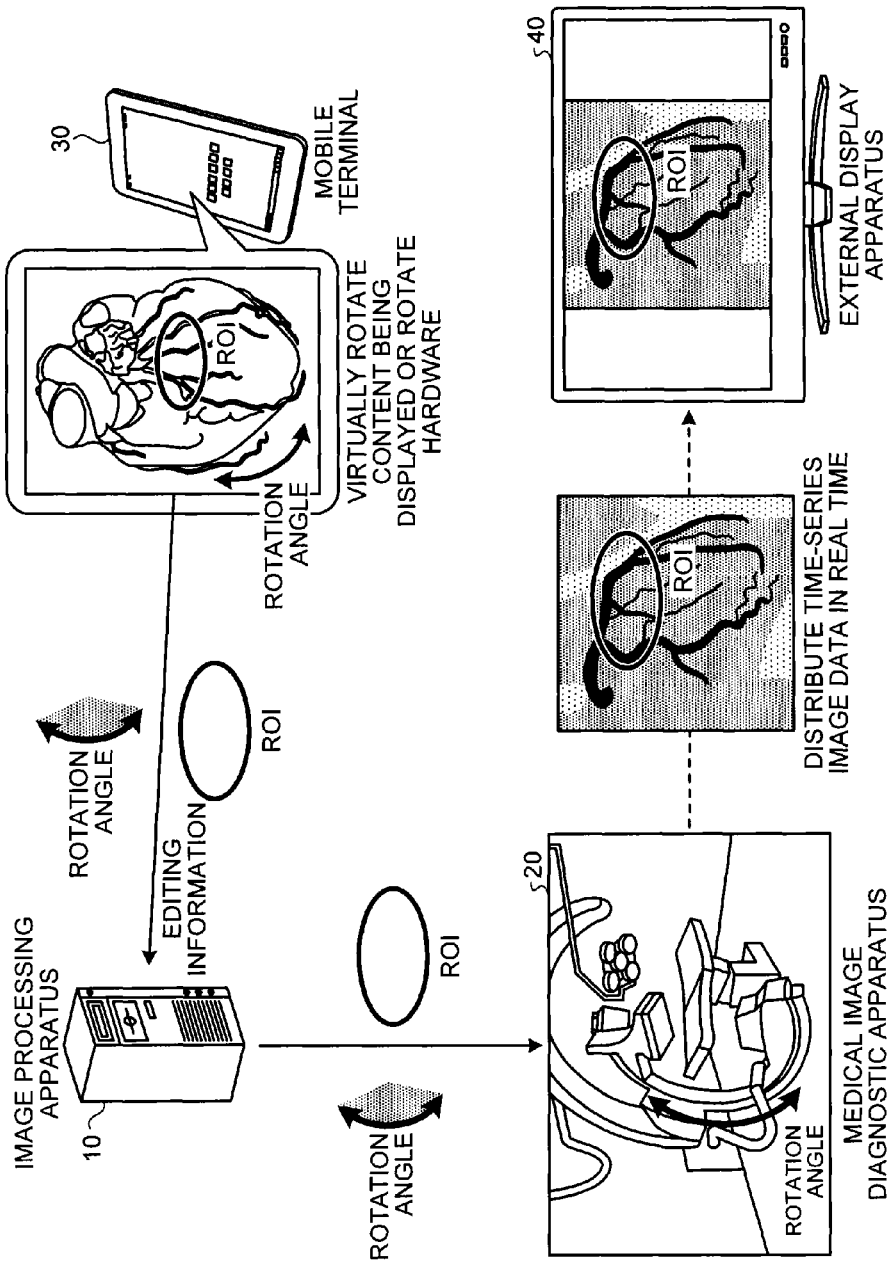
FIG. 6 is a schematic for explaining the concept of the medical image control system according to the second embodiment.

FIGS. 4 to 6 are schematics for explaining the concept of a medical image control system according to a second embodiment.

The medical image control system according to the second embodiment includes an image processing apparatus 10 and an external display apparatus 40, in addition to the medical image diagnostic apparatus 20 and the mobile terminal 30, as illustrated in FIG. 4. A destination of the time-series image data distributed by the medical image diagnostic apparatus 20 in real time is changed to the external display apparatus 40, and other content related to the time-series image data distributed to the external display apparatus 40 (hereinafter, referred to as related content) is distributed from the image processing apparatus 10 to the mobile terminal 30 simultaneously. Information for identifying the related content is transmitted from the medical image diagnostic apparatus 20 to the image processing apparatus 10.

The external display apparatus 40 is a television (TV) or a PC, for example, and has a display unit with a larger screen than the display unit 34 on the mobile terminal 30, for example. The time-series image data distributed by the medical image diagnostic apparatus 20 is displayed on the external display apparatus 40 with a larger screen. The mobile terminal 30 receives related content from the image processing apparatus 10, and displays the related content.

An example of the related content will now be explained. For example, the medical image diagnostic apparatus 20 identifies the position of a catheter by analyzing the time-series image data collected locally, through image processing, and identifies a region of a coronary artery to be treated from the identified position of the catheter. The medical image diagnostic apparatus 20 then notifies the image processing apparatus 10 of a coronary artery ID indicating the identified region of the coronary artery. The image processing apparatus 10 then retrieves image data that is an analysis result of the coronary artery identified by the coronary artery ID from past image data related to the same subject and stored locally, and transmits the retrieved image data to the mobile terminal 30 as related content. As a result, time-series image data of the region of the coronary artery currently being treated is displayed on the external display apparatus 40 with a larger screen, and a result of a past analysis of the region of the coronary artery of the same patient is displayed on the mobile terminal 30. The user of the mobile terminal 30 can then check the time-series image data representing the current treatment, while referring to the result of a past analysis performed on the region of the coronary artery of the patient currently being treated. This embodiment is effective when the display unit 34 on the mobile terminal 30 is small, for example.

As another application, the medical image control system according to the second embodiment controls to synchronize time-series image data and related content distributed in real time, as illustrated in FIG. 5.

For example, the image processing apparatus 10 controls to synchronize the positions where the time-series image data and the related content distributed in real time are displayed using position information included in the time-series image data distributed in real time (e.g., a region being treated or an observation direction). For example, the medical image diagnostic apparatus 20 identifies a region of the coronary artery being treated, notifies the image processing apparatus 10 of the coronary artery ID, and notifies the image processing apparatus 10 of the information about the angle of the C-arm of the medical image diagnostic apparatus 20 being an X-ray diagnostic apparatus. The image processing apparatus 10 then retrieves image data that is an analysis result of the coronary artery identified by the coronary artery ID from the past image data related to the same subject and locally stored, and generates image data from the retrieved image data based on the notified angle of the C-arm. The image processing apparatus 10 then distributes the generated image data to the mobile terminal 30.

As a result, time-series image data representing the region of the coronary artery currently being treated is displayed on the external display apparatus 40 with a larger screen in real time, and a result of a past analysis conducted on the region of the coronary artery of the same patient is displayed on the mobile terminal 30 as an analysis result observed from the same observation direction. In other words, an image of an analysis result having positions to be displayed synchronized is distributed to the mobile terminal 30.

Furthermore, for example, the image processing apparatus 10 controls to synchronize the timing at which the time-series image data and the related content distributed in real time are displayed, using temporal information included in the time-series image data distributed in real time (e.g., biological information such as an electrocardiogram (ECG) or respiration). For example, the medical image diagnostic apparatus 20 acquires the ECG of the subject, and transmits the ECG (or the timing of a major wave (e.g., R wave)) to the image processing apparatus 10. The image processing apparatus 10 then controls so that the past image data related to the same subject is displayed at the timing of the ECG received from the medical image diagnostic apparatus 20. The image processing apparatus 10 then distributes the image data having timing controlled to the mobile terminal 30.

As a result, time-series image data of the region of the coronary artery currently being treated is displayed in real time on the external display apparatus 40 with a larger screen, and a past analysis result of the region of the coronary artery of the same patient is displayed on the mobile terminal 30 in a manner synchronized with the time-series image data at the same ECG timing. In other words, an image of an analysis result having displayed timing synchronized is distributed to the mobile terminal 30.

The positional synchronization or the timing synchronization may be controlled to be achieved in all of or some of the console monitor of the medical image diagnostic apparatus 20, the display of the mobile terminal 30, and the display of the external display apparatus 40. Furthermore, all types of information may be synchronized, or only a part of information may be synchronized. Furthermore, the synchronization may be achieved between the same types of content, or between different types of content.

As another application, in the medical image control system according to the second embodiment, the mobile terminal 30 controls the time-series image data currently being displayed on the external display apparatus 40 via the image processing apparatus 10 or the medical image diagnostic apparatus 20, as illustrated in FIG. 6. In other words, when an image capturing condition is entered or time-series image data is edited on the mobile terminal 30, the information is transferred to the medical image diagnostic apparatus 20 via the image processing apparatus 10. By causing the medical image diagnostic apparatus 20 to capture or to edit an image based on the information, the control applied from the mobile terminal 30 is reflected to the time-series image data distributed in real time from the medical image diagnostic apparatus 20 to the external display apparatus 40.

For example, the mobile terminal 30 receives an operation for designating an angle of the C-arm (by rotating the volume rendering image currently being replayed or rotating the mobile terminal 30 having a gyrosensor) or an operation of drawing an ROI on the time-series image data distributed by the image processing apparatus 10, and transmits the information thus received to the image processing apparatus 10, as illustrated in FIG. 6. When the information is received, the image processing apparatus 10 transfers the information thus received to the medical image diagnostic apparatus 20. The medical image diagnostic apparatus 20 then reflects the information designating an angle of the C-arm transferred by the image processing apparatus 10 to the image capturing condition before capturing an image, for example. The medical image diagnostic apparatus 20 also reflects the ROI transferred by the image processing apparatus 10 to the time-series image data currently being distributed, for example. The medical image diagnostic apparatus 20 then displays the time-series image data collected based on the new image capturing conditions on the console monitor, and distributes the time-series image data to the external display apparatus 40 in real time. The ROI drawn on the mobile terminal 30 is then displayed in the time-series image data.

Figure 7:
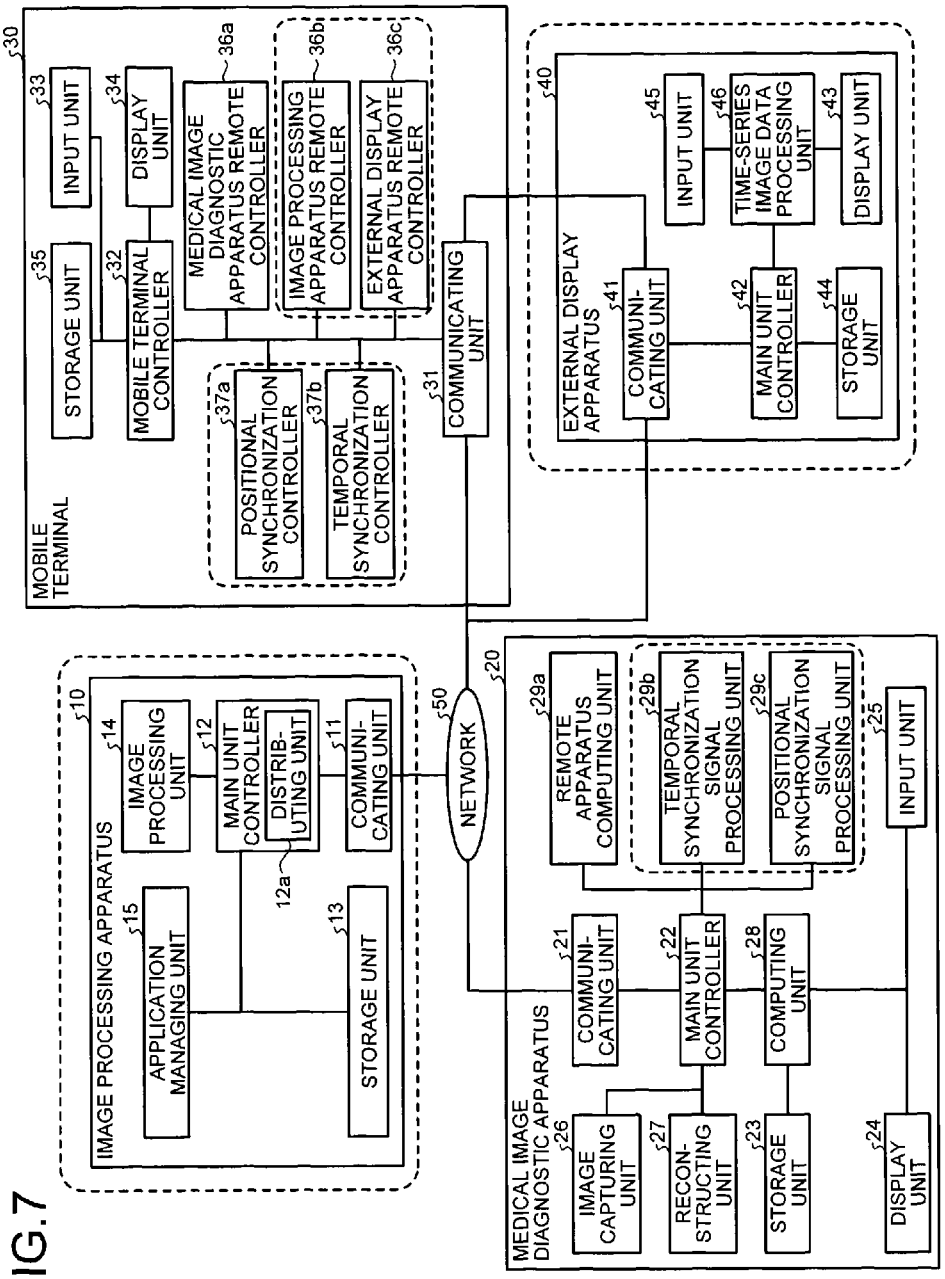
FIG. 7 is a schematic for explaining an exemplary configuration of the medical image control system according to the second embodiment.

FIG. 7 is a schematic for explaining an exemplary configuration of the medical image control system according to the second embodiment. In FIG. 7, the apparatuses and the units surrounded by dotted lines are added to the exemplary configuration according to the first embodiment. As illustrated in FIG. 7, the medical image diagnostic apparatus 20 further includes a temporal synchronization signal processing unit 29b and a positional synchronization signal processing unit 29c.

The temporal synchronization signal processing unit 29b performs a process of synchronizing timing for displaying the time-series image data distributed to the external display apparatus 40 and the related content distributed to the mobile terminal 30. Specifically, the temporal synchronization signal processing unit 29b transmits temporal information of an object represented in the time-series image data to the image processing apparatus 10. For example, the temporal synchronization signal processing unit 29b acquires an ECG of the subject, and transmits the ECG (or the timing of a major wave (e.g., R-wave)) to the image processing apparatus 10.

The positional synchronization signal processing unit 29c performs a process of synchronizing positions where the time-series image data distributed to the external display apparatus 40 is displayed and where the related content distributed to the mobile terminal 30 is displayed. Specifically, the positional synchronization signal processing unit 29c transmits position information of an object represented in the time-series image data to the image processing apparatus 10. For example, the positional synchronization signal processing unit 29c identifies a region being treated and an observation direction, and transmits the information to the image processing apparatus 10. When only the temporal display synchronization, not both of the positional display synchronization and the temporal display synchronization, is to be achieved, information of the region being treated identified by the positional synchronization signal processing unit 29c may be provided to the temporal synchronization signal processing unit 29b, and the temporal synchronization signal processing unit 29b may notify the image processing apparatus 10 of the information as required.

As illustrated in FIG. 7, the mobile terminal 30 further includes an image processing apparatus remote controller 36b, an external display apparatus remote controller 36c, a positional synchronization controller 37a, and a temporal synchronization controller 37b.

The image processing apparatus remote controller 36b remotely controls the image processing apparatus 10 by receiving an operation related to the image processing apparatus 10, and transmitting the control information indicating the received operation to the image processing apparatus 10, in the same manner as the medical image diagnostic apparatus remote controller 36a. For example, the image processing apparatus remote controller 36b receives an operation related to related content, and transmits the control information indicating the received operation to the image processing apparatus 10.

The external display apparatus remote controller 36c remotely controls the external display apparatus 40 by receiving an operation related to the external display apparatus 40, and transmitting the control information indicating the received operation to the external display apparatus 40, in the same manner as the medical image diagnostic apparatus remote controller 36a. The mobile terminal 30 and the external display apparatus 40 may be connected directly. In such a case, the mobile terminal 30 functions as a so-called remote controller for operating the external display apparatus 40.

For a piece of related content to be replayed on the mobile terminal 30, the positional synchronization controller 37a control synchronization of positions where the content is displayed, and the temporal synchronization controller 37b control a synchronization of timing at which the content is displayed. Explained in sequence charts to be explained later is an example in which the image processing apparatus 10 controls the synchronization of positions where content is displayed, and the synchronization of timing at which the content is displayed. In other words, explained is an example in which the image processing apparatus 10 synchronizes positions where and timing at which the content is displayed before distributing the related content to the mobile terminal 30. However, the embodiment is not limited thereto, and the mobile terminal 30 may control the positional synchronization of where the content is displayed and the temporal synchronization at which the content is displayed. For example, the positional synchronization controller 37a and the temporal synchronization controller 37b may respectively receive position information and temporal information, as well as related content from the image processing apparatus 10, and may control replaying the related content using the position information and the temporal information.

As illustrated in FIG. 7, the image processing apparatus 10 includes a communicating unit 11, a main unit controller 12, a storage unit 13, an image processing unit 14, and an application managing unit 15. The communicating unit 11 is an interface on the image processing apparatus 10 connecting the in-hospital LAN. The communicating unit 21 connects to the hospital LAN or to the Internet external to the hospital via network devices such as a hub, and communicates with the medical image diagnostic apparatus 20 and the mobile terminal 30.

The main unit controller 12 is an electronic circuit such as a CPU or an MPU or an integrated circuit such as an ASIC or an FPGA, and controls the overall processing units included in the image processing apparatus 10. The main unit controller 12 includes a distributing unit 12a. The distributing unit 12a identifies a piece of related content from a group of content stored in the storage unit 13 based on information received from the medical image diagnostic apparatus 20 (for example, an examination ID, a patient ID, or the like may be received in addition to the position information), and distributes the identified related content in real time to the mobile terminal 30 using a push-based technology. The distributing unit 12a may be realized using a known streaming technology or progressive download technology, for example.

The distributing unit 12a controls distribution of the related content based on the position information received from the medical image diagnostic apparatus 20 so that an object represented in the related content distributed to the mobile terminal 30 is positionally synchronized with the object represented in the time-series image data distributed to the external display apparatus 40. The distributing unit 12a controls distribution of the related content based on the temporal information received from the medical image diagnostic apparatus 20 so that an object represented in the related content distributed to the mobile terminal 30 is temporally synchronized with the object represented in the time-series image data distributed to the external display apparatus 40.

The storage unit 13 is a hard disk, a semiconductor memory, or the like, and stores therein various types of information in the image processing apparatus 10. The image processing unit 14 applies image processing to image data input to the image processing apparatus 10. The application managing unit 15 manages applications installed in the image processing apparatus 10. For example, the application managing unit 15 starts an application for an analysis, and executes an analysis on an image data input to the image processing apparatus 10. In the second embodiment, the result of the analysis is accumulated in the storage unit 13.

As illustrated in FIG. 7, the external display apparatus 40 includes a communicating unit 41, a main unit controller 42, a display unit 43, a storage unit 44, an input unit 45, and a time-series image data processing unit 46. The communicating unit 41 is an interface on the external display apparatus 40, connects to the in-hospital LAN or to the Internet, and communicates with the mobile terminal 30 and the medical image diagnostic apparatus 20.

The main unit controller 42 is an electronic circuit such as a CPU or an MPU or an integrated circuit such as an ASIC or an FPGA, and controls the overall processing units included in the external display apparatus 40. While the display unit 43 is a monitor, and in the second embodiment, it is assumed that the display unit 43 has a larger screen than the display unit 34 on the mobile terminal 30, the embodiment is not limited thereto. The storage unit 44 is a hard disk, a semiconductor memory, or the like, and stores therein various types of information in the external display apparatus 40. The input unit 45 is a remote controller, a mouse, a keyboard, a trackball, and the like, and receives an operation for the external display apparatus 40 from an operator.

The time-series image data processing unit 46 receives time-series image data distributed by the medical image diagnostic apparatus 20, and replays the received time-series image data in real time. The time-series image data processing unit 46 also receives an operation for editing the time-series image data being replayed, and reflects the editing operation thus received to the time-series image data. Such an editing operation can be performed independently from the time-series image data captured by the medical image diagnostic apparatus 20. The time-series image data processing unit 46 may also receive an editing operation from the mobile terminal 30.

Figure 8:
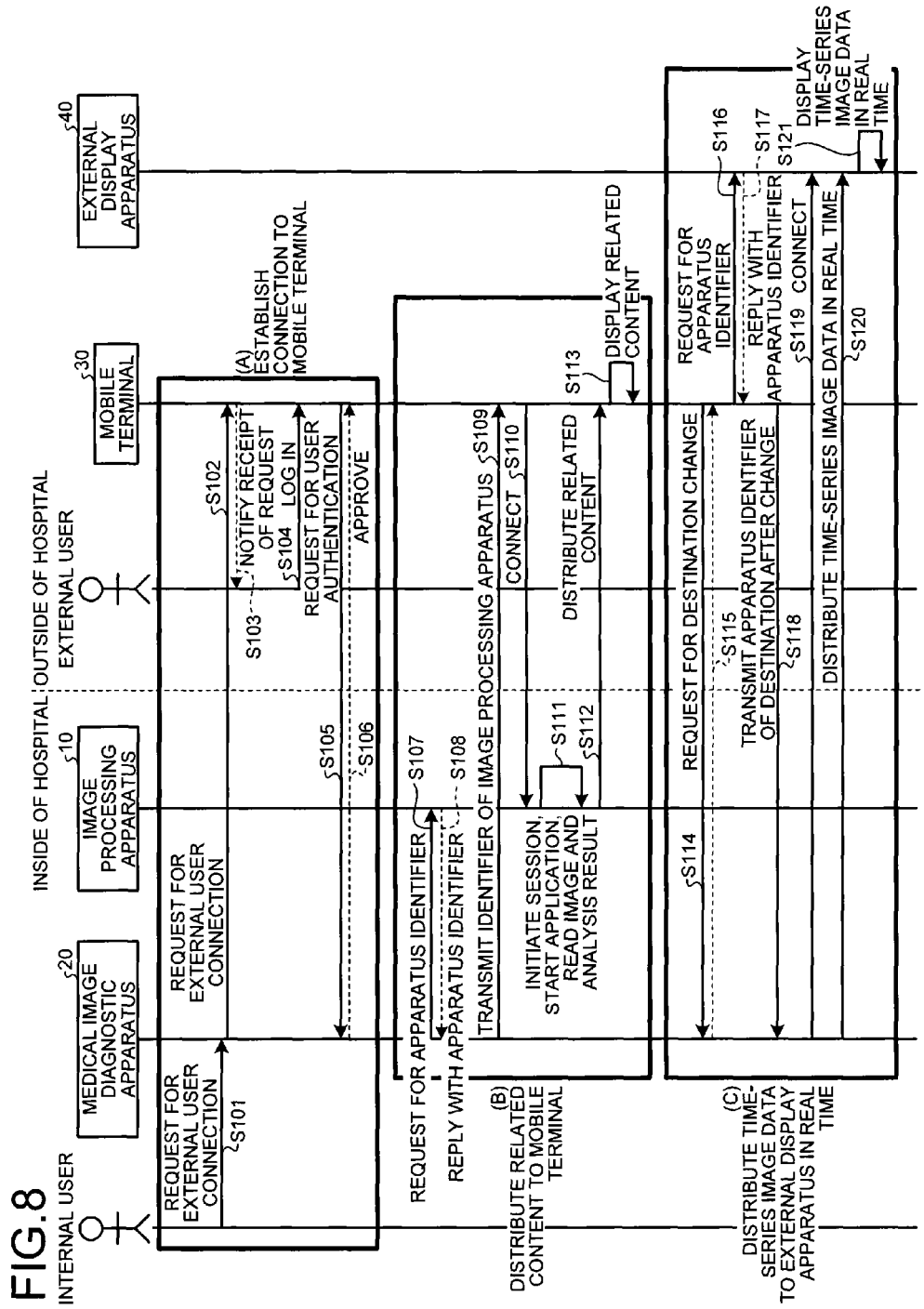
FIG. 8 is a sequence chart illustrating an example of a process in the second embodiment.

FIGS. 8 and 9 are sequence charts illustrating an example of the processes in the second embodiment. FIG. 8 mainly illustrates a process of establishing a connection between these apparatuses, and FIG. 9 mainly illustrates a process of distributing content. In actual operations, these processes are generally performed continuously, because content is distributed after a connection is established between the apparatuses.

(A) is a process in which a connection is established to the mobile terminal 30. As illustrated in FIG. 8, an operator operating on the medical image diagnostic apparatus 20 (in FIG. 8, an "internal user") inputs an "external user connection request" requesting the medical image diagnostic apparatus 20 to establish a connection to an external user (Step S101). For example, the operator inputs an "external user connection request", along with the email address of the external user.

The medical image diagnostic apparatus 20 then transmits the "external user connection request" to the mobile terminal 30 used by the external user (Step S102). For example, the medical image diagnostic apparatus 20 transmits the "external user connection request" to the email address input by the internal user via an email.

The mobile terminal 30 then notifies the user of the mobile terminal 30 of reception of the "external user connection request" (Step S103). The external user then performs a log-in operation on the mobile terminal 30 (Step S104), and a user authentication is performed between the mobile terminal 30 and the medical image diagnostic apparatus 20 (Steps S105 and S106). For example, the external user receiving the email of the "external user connection request" transmits a "user authenticating request" (for example, an ID and a password) to the medical image diagnostic apparatus 20, by opening the email and accessing the URL specified in the email, for example. When the user authentication succeeds, the medical image diagnostic apparatus 20 transmits an approval to the mobile terminal 30.

(B) is a process of distributing related content to the mobile terminal. As illustrated in FIG. 8, the medical image diagnostic apparatus 20 requests an apparatus identifier from the image processing apparatus 10 (Step S107), and receives a reply (Step S108). The medical image diagnostic apparatus 20 then transmits the apparatus identifier of the image processing apparatus 10 to the mobile terminal 30 (Step S109).

The mobile terminal 30 connects to the image processing apparatus 10 by designating the apparatus identifier thus received (Step S110). For example, the mobile terminal 30 stores therein an apparatus identifier and a URL in an associated manner, and connects to the image processing apparatus 10 by designating and accessing the URL stored in a manner associated with the received apparatus identifier.

Upon receiving a connection from the mobile terminal 30, the image processing apparatus 10 initiates a session with the mobile terminal 30, starts an application, and reads a piece of related content (e.g. image data, an analysis result) (Step S111). Although not illustrated in FIG. 8, the image processing apparatus 10 may receive information for identifying the related content from the medical image diagnostic apparatus 20 in advance, and identify the related content based on the information, for example. For example, the image processing apparatus 10 receives information such as an examination ID and a patient ID and information about a region being treated from the medical image diagnostic apparatus 20 in advance, and retrieves past image data or analysis results of the same patient based on the information. The image processing apparatus 10 then reads the retrieved image data or the retrieved analysis results as related content.

The image processing apparatus 10 then distributes the related content to the mobile terminal 30 (Step S112). The mobile terminal 30 displays the distributed related content on the display unit 34 (Step S113). The related content may be still image data, time-series image data, patient information, an electronic medical record, or an examination report, for example.

(C) is a process of distributing a time-series image data to the external display apparatus in real-time. As illustrated in FIG. 8, the mobile terminal 30 transmits a "destination change request", requesting to change the destination of the distribution, to the medical image diagnostic apparatus 20 (Step S114). The medical image diagnostic apparatus 20 then responds to the request (Step S115).

The mobile terminal 30 then requests an apparatus identifier from the external display apparatus 40 (Step S116), and receives a reply (Step S117). The mobile terminal 30 then transmits the apparatus identifier identifying the external display apparatus 40 which is a changed destination to the medical image diagnostic apparatus 20 (Step S118). If the medical image diagnostic apparatus 20 does not have any information for accessing the external display apparatus 40, the mobile terminal 30 may transmit the information for accessing the external display apparatus 40 when the mobile terminal 30 transmits the apparatus identifier at Step S118, for example.

The medical image diagnostic apparatus 20 then connects to the external display apparatus 40 notified by the mobile terminal 30 (Step S119), and starts distributing time-series image data in real time (Step S120). The external display apparatus 40 then replays the time-series image data distributed by the medical image diagnostic apparatus 20 on the display unit 43 (Step S121).

(A) in FIG. 9 is a process of synchronizing positions where the content is displayed. As illustrated in FIG. 9, the medical image diagnostic apparatus 20 extracts a coronary artery currently being treated, by analyzing the time-series image data (Step S201). The medical image diagnostic apparatus 20 then notifies the image processing apparatus 10 of position information indicating the coronary artery, such as a coronary artery ID or an angle of the C-arm (Step S202). The medical image diagnostic apparatus 20 may also provide other information required to identify related content.

The image processing apparatus 10 then retrieves an analysis result of the coronary artery thus specified from past image data accumulated locally or in other apparatuses, using the information notified by the medical image diagnostic apparatus 20 (Step S203). At this time, the image processing apparatus 10 adjusts the angle of the coronary artery represented in the analysis result based on the angle of the C-arm received from the medical image diagnostic apparatus 20, so that objects represented in the analysis result distributed to the mobile terminal 30 are positionally synchronized with the objects represented in the time-series image data distributed to the external display apparatus 40.

The image processing apparatus 10 then distributes the analysis result to the mobile terminal 30 (Step S204). The mobile terminal 30 then display the analysis result on the display unit 34 (Step S205). The medical image diagnostic apparatus 20 distributes time-series image data to the external display apparatus 40 in real time (Step S206), and the external display apparatus 40 displays the time-series image data on the display unit 43 (Step S207). In this manner, objects represented in the analysis result distributed to the mobile terminal 30 are positionally synchronized with the objects represented in the time-series image data distributed to the external display apparatus 40.

(B) is a process of synchronizing the timing at which the content is displayed. As illustrated in FIG. 9, the medical image diagnostic apparatus 20 acquires an ECG from the subject (Step S208). The medical image diagnostic apparatus 20 then notifies the image processing apparatus 10 of the temporal information such as the ECG (Step S209). The medical image diagnostic apparatus 20 may also provide other information required to identify related content.

The image processing apparatus 10 then retrieves time-series image data being an analysis result from the past image data accumulated locally or in other apparatuses, using the information notified by the medical image diagnostic apparatus 20 (Step S210). At this time, the image processing apparatus 10 adjusts the timing at which objects represented in the time-series image data of the analysis result are displayed, so that objects represented in the time-series image data of the analysis result distributed to the mobile terminal 30 are temporally synchronized with the objects represented in the time-series image data distributed to the external display apparatus 40, in other words, so that these objects match the ECG received from the medical image diagnostic apparatus 20.

The image processing apparatus 10 then distributes the analysis time-series image data having display timing matched to the ECG to the mobile terminal 30 (Step S211). The mobile terminal 30 then displays the time-series image data on the display unit 34 (Step S212). The medical image diagnostic apparatus 20 distributes time-series image data to the external display apparatus 40 in real time (Step S213), and the external display apparatus 40 displays the time-series image data on the display unit 43 (Step S214). In this manner, objects represented in the time-series image data of the analysis result distributed to the mobile terminal 30 are temporally synchronized with the objects represented in the time-series image data distributed to the external display apparatus 40.

Variation of Second Embodiment

The second embodiment is not limited to the embodiment described above. For example, an exemplary configuration of the medical image control system according to the second embodiment is illustrated in FIG. 7. However, the configuration including all of these apparatuses and the units is not mandatory, and a configuration having only some of the apparatuses and the units is still possible. Furthermore, for example, a synchronizations of positions where or timing at which content is displayed is not a mandatory feature.

Furthermore, the processes illustrated in FIGS. 8 and 9 may be modified as appropriate. For example, the authenticating process explained in (A) in FIG. 8 may be omitted, or modified to a different process. For example, the process may be modified to a process for requesting an external user to establish a connection. Furthermore, the process illustrated in (B) in FIG. 8 may start from distributing time-series image data in real time to the mobile terminal 30, for example, and then the destination may be changed to the external display apparatus 40 in response to a request issued by the mobile terminal 30. In such a case, the external display apparatus 40 may receive distribution of time-series image data reflected with an edition made on the mobile terminal 30. Furthermore, only one of the processes explained in (A) and (B) in FIG. 9 may be performed, for example. Furthermore, the information provided to the image processing apparatus 10 as the position information or the temporal information may be changed in any way. Furthermore, the related content and the time-series image data may be displayed oppositely in real time. In other words, time-series image data may be distributed to the mobile terminal 30 in real time, and related content may be distributed to the external display apparatus 40. In such a case, the mobile terminal 30 requests a change of the destination from the image processing apparatus 10.

The external display apparatus 40 does not necessarily need to have a larger screen compared with the mobile terminal 30, and may also be another mobile terminal. Furthermore, explained in the second embodiment is an example where the medical image diagnostic apparatus is provided in singularity, the image processing apparatus is provided in singularity, the mobile terminal is provided in singularity, and the external display apparatus is provided in singularity. However, the embodiment is not limited thereto. In a configuration in which a plurality of medical image diagnostic apparatuses, a plurality of image processing apparatus, a plurality of mobile terminals, and a plurality of external display apparatuses are connected over a network, some of the apparatuses may communicate with each other, and display content after synchronizing the positions where or timing at which the content is displayed. Furthermore, in such a case, a temporary condition of being edited on a given apparatus may be carried over another apparatus. In other words, editing information received on a given apparatus may be transmitted to another apparatus over the network, and may be reflected on the apparatus.

FIG. 10 is a schematic for explaining a variation of the second embodiment. As illustrated in FIG. 10, time-series image data in which an operation site (e.g., a medical front such as an operation room) is captured may be distributed as time-series image data in real time as well. Furthermore, as illustrated in FIG. 10, biological information may be also distributed in real time as well. As illustrated in FIG. 10, for example, the external display apparatus 40 receives all of time-series image data in which a subject is captured, time-series image data in which an operation site is captured, and biological information via a real-time distribution, and display all of the time-series image data and the information in a single display.

Advantageous Effects Achieved by Second Embodiment

As described above, according to the second embodiment, because time-series image data distributed in real time is received by and displayed on one apparatus and distribution of content related to the time-series image data is received and displayed on another apparatus (for example, on a mobile terminal), a user of the mobile terminal can support medical interventions remotely, while looking at a plurality of pieces of information. Furthermore, content displayed on the mobile terminal, the medical image diagnostic apparatus, and the external display apparatus can be synchronized, and editions and operations can be shared among the content displayed on the mobile terminal, the medical image diagnostic apparatus, and the external display apparatus, centering around a server such as the image processing apparatus.

Third Embodiment

A medical image control system according to a third embodiment ensures safety by limiting functions that are made available for a remote control. Specifically, the medical image diagnostic apparatus 20 (local side) retains a risk table in which a risk level is associated with an operation type and a limitation applied to such an operation. When the medical image diagnostic apparatus 20 receives an operation from the mobile terminal 30 (remote side), the medical image diagnostic apparatus 20 refers to the risk table and controls the operation performed by the operator (remote user) of the mobile terminal 30. The medical image control system according to the third embodiment has the same configuration as the medical image control system according to the first and the second embodiment, and can be applied to the medical image control system according to first and the second embodiment.

FIG. 11 is a schematic for explaining the risk table in the third embodiment. The exemplary risk table illustrated in FIG. 11 is merely an example, and may be modified in any way depending on how the system is operated. For example, the medical image diagnostic apparatus 20 stores the risk table in the storage unit 23. The risk table makes an association between a risk level, a function (operation), and a limitation applied to the operation, for example, as illustrated in FIG. 11. For example, a risk level "A" is a level that could be extremely harmful to a human body, "B" is a level that could be harmful to a human body, and "C" is a level less harmful to a human body.

For example, "start capturing image" as a function (operation) is associated with the risk level "A". For example, if the medical image diagnostic apparatus 20 starts capturing an image at timing not intended by a local user, the C-arm may suddenly starts operating or irradiation of X rays may be started suddenly. Therefore, a risk to a human body is extremely high. Hence, it is preferable to apply a limitation to a remote user for such an operation. Therefore, "operation not permitted" is stored in a manner associated with the "start capturing image" in the risk table. Similarly, for example, "change image conditions while capturing image" is associated with the risk level "B" as a function (operation). A remote user is permitted to make such an operation, provided that the remote user is approved of such an operation by a local user. For example, "make operations on stored image" is associated with the risk level "C" as a function (operation). Because such an operation is less harmful, it is not necessary to apply a limitation to a remote user. Therefore, "operation permitted" is stored in the risk table in a manner associated with "make operations on stored image".

In such a configuration, when control information is received from the mobile terminal 30, the reflecting unit 22b in the medical image diagnostic apparatus 20 refers to the risk table, identifies the risk level of the operation designated in the control information, and controls to reflect a limitation to the process performed by the medical image diagnostic apparatus 20 based on the limitation associated with the identified risk level.

FIGS. 12 and 13 are schematics for explaining limitations in the functions made available for remote control in the third embodiment. As illustrated in FIG. 12, it is assumed that a local user operating the medical image diagnostic apparatus 20 draws an ROI on time-series image data being replayed on the console monitor, for example (S1). The time-series image data on which the ROI is drawn is distributed to the mobile terminal 30 (S2). The mobile terminal 30 then receives an edition of the ROI as an editing operation to the time-series image data, for example (S3), and transfers the editing information thus received to the medical image diagnostic apparatus 20 (S4). At this time, the reflecting unit 22b according to the third embodiment refers to the risk table, evaluates the risk level of the operation (edition of the ROI) specified in the control information, and determines that the risk level is "B", for example (S5).

In the third embodiment, the risk level "B" is a level permitting an operation to be executed, provided that a local user approves of such an operation. Therefore, the reflecting unit 22b displays the ROIs in different visual attributes (e.g., in different colors, different shapes, or combination thereof), for example, on the time-series image data replayed on the console monitor to enable the ROI drawn by the local user and the ROI edited by the remote user to be distinguished (S6). For example, in FIG. 12, the reflecting unit 22b displays a comparative image. In the comparative image, the ROI drawn by the local user is represented as an oval in a dotted line, and the ROI edited by the remote user is represented as a rectangle in a solid line. When the local user approves, the local user can distinguish and compare these ROIs.

The local user then looks at the comparative image, determines if the edition of the ROI made by the remote user is to be approved, and enters the result of the determination to the medical image diagnostic apparatus 20. The reflecting unit 22b then displays a resultant display window indicating final resultant ROI, for example, based on whether the local user approves. For example, when the edition is approved, the reflecting unit 22b executes subsequent processes using the ROI edited by the remote user. By contrast, if the edition is not approved, the reflecting unit 22b executes subsequent processes using the ROI drawn by the local user.

Furthermore, as illustrated in FIG. 13, for example, when an editing operation of the ROI is managed with the risk level "A" in the risk table, because the risk level "A" is a level not permitting any operations by a remote user, the reflecting unit 22b rejects the edition made by the remote user, and executes the subsequent process using the ROI drawn by the local user, without using the ROI edited by the remote user (S6). For example, the reflecting unit 22b transfers the original image (in other words, the image including the ROI drawn by the local user) to the mobile terminal 30 (S7). The reflecting unit 22b may also transfer notification information indicating that such an operation was not accepted, for example.

The third embodiment is not limited thereto. FIG. 14 is a schematic for explaining a variation of the limitation in the functions made available for remote control in the third embodiment. For example, before distributing time-series image data to the mobile terminal 30, the distributing unit 22a in the medical image diagnostic apparatus 20 may refer to the risk table, and may distribute an operation window in which operations are limited as an operation window for receiving an operation from the mobile terminal 30.

For example, in FIG. 14, it is assumed that an operation window for receiving an operation is displayed on the console monitor of the medical image diagnostic apparatus 20 or the display unit 34 of the mobile terminal 30, and the operation window includes operation buttons each of which is for each function. For example, it is assumed that a "function 1" is an operation button for executing an operation at a risk level "A", a "function 2" is an operation button for executing an operation at a risk level "B", and a "function 3" is an operation button for executing an operation at a risk level "C".

For example, because every local operation is permitted, the medical image diagnostic apparatus 20 displays all of the operation buttons including the "function 1", the "function 2", and the "function 3" on the console monitor. Before distributing time-series image data to the mobile terminal 30, the distributing unit 22a refers to the risk table, and evaluates the risk level of each of the functions to be shown in the operation window on the mobile terminal 30 (S1). The distributing unit 22a then distributes an operation window with a change applied so that the operation button for the function corresponding to the risk level "A" is hidden on the mobile terminal 30 (or in a manner not permitting any operation) to the mobile terminal 30. For example, in FIG. 14, in the operation window displayed on the mobile terminal 30, the operation button for the "function 1" is hidden, and the operation buttons for the "function 2" and the "function 3" are shown (S2). Therefore, the remote user operates the functions at the risk level "B" or "C", and transfers the result of editing (S3).

The medical image diagnostic apparatus 20 may also stores therein a history of operations performed by a local user and a remote user, a history indicating which operation performed by a local user and a remote user is actually applied, which local user approved an operation, and the like. In such a case, the medical image diagnostic apparatus 20 may compare an operation performed by a local user with an operation performed by a remote user, and evaluate the difference, for example. Furthermore, the medical image diagnostic apparatus 20 may also receive an operation for reverting a process and reproduce a previous condition. For example, if a remote user makes an operation (for example, an operation at the risk level "C") while the local user is out of the seat, the local user might review the history accumulated in the medical image diagnostic apparatus 20, and may specify to revert the process to a condition applied with the latest operation performed by the local user him/herself, for example. When a designation of the history is received, the medical image diagnostic apparatus 20 reproduces a condition in the designated history.

Explained in the third embodiment is an example in which the medical image diagnostic apparatus 20 retains a risk table and limits an operation performed by a remote user. However, the embodiment is not limited thereto. For example, an apparatus that is different from the medical image diagnostic apparatus 20 may intermediate communications between the medical image diagnostic apparatus 20 and the mobile terminal 30, and may limit operations performed by a remote user based on the risk table retained by such an apparatus.

Other Embodiments

The medical image control system and the mobile terminal according to the embodiment are not limited to the embodiments described above.

Explained in the embodiments described above is an example in which the medical image diagnostic apparatus 20 is an X-ray diagnostic apparatus or an X ray CT apparatus. However, the embodiment is not limited thereto. The medical image diagnostic apparatus 20 may also be a magnetic resonance imaging (MRI) apparatus, an ultrasonic diagnostic apparatus, a single photon emission computed tomography (SPECT) apparatus, a positron emission computed tomography (PET) apparatus, a SPECT-CT apparatus, or a PET-CT apparatus. Furthermore, the medical image diagnostic apparatus 20 may be replaced with a radiation treatment apparatus such as that used for the Gamma Knife or the CyberKnife. Furthermore, the functions explained to be included in the medical image diagnostic apparatus 20 in the embodiments may be included in a different apparatus that is independent from the medical image diagnostic apparatus.

For example, this different apparatus may be provided with functions of distributing time-series image data in real time, achieving temporal synchronization and positional synchronization, without processing units such as an image capturing unit.

Furthermore, explained in the embodiment is an example in which the image processing apparatus 10 is a workstation (WS) in which applications for image processing and the like are installed. However, the embodiment is not limited thereto. The image processing apparatus 10 may be replaced with an image storage apparatus when a picture archiving and communication system (PACS) is deployed, or replaced with a radiotherapy planning apparatus.

Furthermore, explained in the embodiment is an example in which the external display apparatus 40 is a TV apparatus or a PC. However, the embodiment is not limited thereto. For example, the external display apparatus 40 may be replaced with a mobile terminal that is separate from the mobile terminal 30 on which the related content is displayed.

Furthermore, locations where the medical image diagnostic apparatus 20 is installed or where the mobile terminal 30 is used is not limited to hospitals, and may also be in an ambulance or outdoors such as a disaster site, for example, as long as the location has an environment in which the medical image diagnostic apparatus 20 and the mobile terminal 30 can communicate with each other directly or indirectly. Furthermore, the second embodiment may also be realized similarly as long as such a location has an environment in which the medical image diagnostic apparatus 20 and the mobile terminal 30 can communicate with the image processing apparatus 10 and the external display apparatus 40 directly or indirectly.

Furthermore, explained in the embodiment is an example in which time-series image data distributed in real time is time-series image data collected and generated by the medical image diagnostic apparatus 20. However, the embodiment is not limited thereto. The time-series image data distributed in real time may also be replaced with time-series image data capturing an Angio room, an operating room, or inside of an ambulance, for example. Such a configuration is achievable in an environment where the apparatus distributing time-series image data in real time and the mobile terminal 30 can communicate with each other directly or indirectly. Furthermore, explained in the embodiment is an example in which time-series image data is replayed by the mobile terminal 30. However, the embodiment is not limited thereto. For example, still image data, electronic medical records, examination reports, patient information, or the like may be displayed on the mobile terminal 30. For example, the external display apparatus 40 may display time-series image data in real-time, and the mobile terminal 30 may display information of the patient represented in the time-series image data.

Furthermore, explained in the embodiment is an example in which the medical image diagnostic apparatus 20 and the mobile terminal 30 are connected to each other indirectly over the network 50. However, the embodiment is not limited thereto. The medical image diagnostic apparatus 20 and the mobile terminal 30 may be connected to each other directly.

OTHERS

The units included in the apparatuses are illustrated in the drawings to schematically depict their functionality, and are not necessary configured physically in the manner illustrated in the drawings. In other words, specific configurations in which the apparatuses are distributed or integrated are not limited to those illustrated in the drawings. The whole or a part of the apparatuses may be distributed or integrated functionally or physically in any units depending on various loads or utilization. The whole or a part of the processing functions executed in each of the apparatuses may be realized as a CPU and a computer program parsed and executed by the CPU, or realized as hardware using wired logics.

Furthermore, the image processing method explained in the embodiments may be realized by causing a computer such as a PC or a workstation to execute image processing program created in advance. The image processing program may be distributed over a network such as the Internet. Furthermore, the computer program may be recorded in a computer-readable recording medium such as a hard disk, a flexible disk (FD), a compact disk read-only memory (CD-ROM), a magneto-optical (MO) disk, or a digital versatile disk (DVD), and executed by causing a computer to read the computer program from the recording medium.

The medical image control system and the mobile terminal according to at least one of the embodiments enable a mobile terminal to support a medical intervention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image control system comprising:
   a medical image diagnostic apparatus; and
   a mobile terminal, wherein
   the medical image diagnostic apparatus includes:
      a memory configured to store therein a type of an operation related to the medical image diagnostic apparatus being associated with a limitation applied to the operation;
      collecting circuitry configured to capture a subject based on a predetermined image capturing condition to collect time-series image data;
      distributing circuitry configured to distribute the time-series image data to the mobile terminal at least when the collecting circuitry collects the time-series image data; and
      reflecting circuitry configured to receive control information transmitted from the mobile terminal, and to reflect the received control information to a process performed by the medical image diagnostic apparatus
   the mobile terminal includes:
      replaying circuitry configured to receive the time-series image data distributed by the distributing circuitry, and to replay the received time-series image data; and
      control information transmitting circuitry configured to receive an operation related to the medical image diagnostic apparatus, and to transmit control information indicating the received operation to the medical image diagnostic apparatus,
   the reflecting circuitry is configured to, when control information is received from the mobile terminal, control to reflect a process performed by the medical image diagnostic apparatus based on a limitation associated with a type of an operation indicated by the received control information, and
   the limitation determines whether a type of an operation is permitted or not permitted.

2. The medical image control system according to claim 1, wherein
   the reflecting circuitry is configured to receive setting information of an image capturing condition as the control information, and to reflect the received setting information to the predetermined image capturing condition to be used when the collecting circuitry captures a subject, and
   the control information transmitting circuitry is configured to receive an operation related to the image capturing condition, and to transmit received setting information of the image capturing condition to the medical image diagnostic apparatus.

3. The medical image control system according to claim 1, wherein
   the reflecting circuitry is configured to receive editing information for the time-series image data as the control information, and to reflect the received editing information to time-series image data replayed by the medical image diagnostic apparatus, and
   the control information transmitting circuitry is configured to receive an editing operation for the time-series image data, and to transmit received editing information indicating the editing operation to the medical image diagnostic apparatus.

4. The medical image control system according to claim 1, wherein
   the mobile terminal further includes time-series image data editing circuitry configured to receive an editing operation for the time-series image data replayed by the replaying circuitry, and to reflect the received editing operation to the time-series image data replayed by the replaying circuitry.

5. The medical image control system according to claim 1, wherein
   the memory is further configured to store therein a risk table in which a risk level of a type of an operation is associated with a limitation applied to the operation, and
   the reflecting circuitry is configured to, when the control information is received from the mobile terminal, refer to the risk table, to identify a risk level of an operation specified in the control information, and to control to reflect the operation to a process performed by the medical image diagnostic apparatus based on a limitation associated to the identified risk level.

6. The medical image control system according to claim 1, wherein
   the memory is further configured to store therein a risk table in which a risk level of a type of an operation is associated with a limitation applied to the operation, and
   the distributing circuitry is configured to, before distributing the time-series image data to the mobile terminal, refer to the risk table and distribute an operation window in which operations are limited based on the limitation, as an operation window for receiving the operation on the mobile terminal.

7. A medical image control system comprising:
a medical image diagnostic apparatus;
a managing apparatus;
a mobile terminal; and
a display apparatus, wherein
the medical image diagnostic apparatus includes:
- collecting circuitry configured to capture a subject based on a predetermined image capturing condition to collect time-series image data;
- distributing circuitry configured to distribute the time-series image data to the display apparatus used by a user of the mobile terminal at least when the collecting circuitry collects the time-series image data; and
- notifying circuitry configured to notify the managing apparatus configured to manage a group of related image data of information for identifying related image data related to the time-series image data, the related image data being image data of a past analysis performed on the subject, the managing apparatus includes distributing circuitry configured to distribute the related image data to the mobile terminal based on the information notified by the notifying circuitry, the mobile terminal includes replaying circuitry configured to receive the related time-series image data distributed by the distributing circuitry included in the managing apparatus, and to replay the received related time-series image data, and the display apparatus includes replaying circuitry configured to receive the time-series image data distributed by the distributing circuitry included in the medical image diagnostic apparatus, and to replay the received time-series image data.

8. The medical image control system according to claim 7, wherein
the notifying circuitry included in the medical image diagnostic apparatus is configured to provide information related to a direction in which the medical image diagnostic apparatus captures an image, and
the distributing circuitry included in the managing apparatus is configured to distribute image data generated from three-dimensional image and the information related to the direction in which the image is captured as the related image data.

9. The medical image control system according to claim 8, wherein
the distributing circuitry included in the medical image diagnostic apparatus is configured to, when a request for designating the display apparatus as a destination is received from the mobile terminal, distribute the time-series image data to the designated display apparatus.

10. The medical image control system according to claim 8, wherein
the notifying circuitry included in the medical image diagnostic apparatus is configured to provide position information of an object represented in the time-series image data, together with information for identifying related time-series image data that is related to the time-series image data, and
the distributing circuitry included in the managing apparatus is configured to control distribution of the related time-series image data based on the position information so that an object represented in the related time-series image data to be distributed to the mobile terminal and an object represented in the time-series image data distributed to the display apparatus are positionally synchronized.

11. The medical image control system according to claim 8, wherein
the notifying circuitry included in the medical image diagnostic apparatus is configured to provide temporal information of an object represented in the time-series image data, together with information for identifying related time-series image data that is related to the time-series image data, and
the distributing circuitry included in the managing apparatus is configured to control distribution of the related time-series image data based on the temporal information so that an object represented in the related time-series image data to be distributed to the mobile terminal and an object represented in the time-series image data distributed to the display apparatus are temporally synchronized.

12. The medical image control system according to claim 8, wherein
the display apparatus further includes time-series image data editing circuitry configured to receive an editing operation for the time-series image data replayed by the replaying circuitry, and to reflect the received editing operation to the time-series image data replayed by the replaying circuitry.

13. The medical image control system according to claim 12, wherein
the time-series image data editing circuitry is configured to receive the editing operation from the mobile terminal.

* * * * *